(12) United States Patent
Batt et al.

(10) Patent No.: US 7,479,496 B2
(45) Date of Patent: Jan. 20, 2009

(54) SUBSTITUTED SPIRO AZABICYCLICS AS MODULATORS OF CHEMOKINE RECEPTOR ACTIVITY

(75) Inventors: Douglas G. Batt, Wilmington, DE (US); Dean A. Wacker, Yardley, PA (US); George V. De Lucca, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 550 days.

(21) Appl. No.: 11/060,246

(22) Filed: Feb. 17, 2005

(65) Prior Publication Data

US 2005/0197325 A1 Sep. 8, 2005

Related U.S. Application Data

(60) Provisional application No. 60/545,816, filed on Feb. 19, 2004.

(51) Int. Cl.
*A61K 31/44* (2006.01)
*C07D 215/00* (2006.01)
(52) U.S. Cl. ........................ 514/278; 546/16
(58) Field of Classification Search ............... 546/16; 514/278
See application file for complete search history.

(56) References Cited

U.S. PATENT DOCUMENTS

| | | | |
|---|---|---|---|
| 5,869,496 | A | 2/1999 | Hale et al. |
| 6,011,052 | A | 1/2000 | Padia et al. |
| 6,013,644 | A | 1/2000 | Mills et al. |
| 2005/0192276 | A1 | 9/2005 | Batt et al. |
| 2005/0197325 | A1 | 9/2005 | Batt et al. |
| 2005/0197373 | A1 | 9/2005 | Batt et al. |

FOREIGN PATENT DOCUMENTS

| | | |
|---|---|---|
| WO | WO 94/29309 | 12/1994 |
| WO | WO 97/44329 | 11/1997 |
| WO | WO 98/06703 | 2/1998 |
| WO | WO 99/07351 | 2/1999 |
| WO | WO 99/07678 | 2/1999 |
| WO | WO 99/25686 | 5/1999 |
| WO | WO 99/40913 | 8/1999 |
| WO | WO 99/40914 | 8/1999 |
| WO | WO 00/46196 | 8/2000 |
| WO | WO 00/69815 | 11/2000 |
| WO | WO 00/69820 | 11/2000 |
| WO | WO 02/50019 A2 | 6/2002 |
| WO | WO02/060859 A2 | 8/2002 |
| WO | WO02/070523 A1 | 9/2002 |
| WO | WO 02/081449 A1 | 10/2002 |
| WO | WO03/091245 A1 | 11/2003 |
| WO | WO03/092568 A1 | 11/2003 |
| WO | WO03/093231 A2 | 11/2003 |
| WO | WO03/099773 A1 | 12/2003 |
| WO | WO03/101970 A1 | 12/2003 |
| WO | WO03/105853 A1 | 12/2003 |
| WO | WO2004/007472 A1 | 1/2004 |
| WO | WO2004/009550 A1 | 1/2004 |
| WO | WO2004/009588 A1 | 1/2004 |
| WO | WO 2004/010942 A2 | 2/2004 |
| WO | WO2004/010943 A2 | 2/2004 |
| WO | WO 2004/011418 A1 | 2/2004 |
| WO | WO 2004/011427 A2 | 2/2004 |
| WO | WO 2004/011443 A1 | 2/2004 |
| WO | WO2004/012671 A2 | 2/2004 |

OTHER PUBLICATIONS

Obach R. S., Drug-drug interactions: An important negative attribute in drugs, Drugs of Today, 39(5), 301-38, (2003).*
U.S. Appl. No. 11/060,250, filed Feb. 17, 2005, Batt et al.
Forbes, Ian T. et al.,"CCR2B Receptor Antagonists:Conversion of a Weak HTS Hit to a Potent Lead Compound", Bioorg. Med. Chem. Lett. vol. 10, pp. 1803-1806 (2000).
Mirzadegan, Tara et al., "Indentification of the Binding Site for a Novel Class of CCR2b Chemokine Receptor Antagonists", The Journal of Biological Chemistry vol. 275 No. 33, pp. 25562-25571 (2000).

(Continued)

*Primary Examiner*—Rei-tsang Shiao
(74) *Attorney, Agent, or Firm*—Terence J. Bogie

(57) ABSTRACT

The present application describes modulators of CCR3 of formula (Ia) and (Ib):

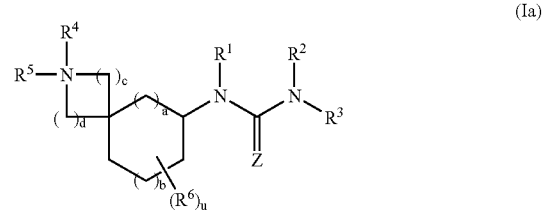

(Ia)

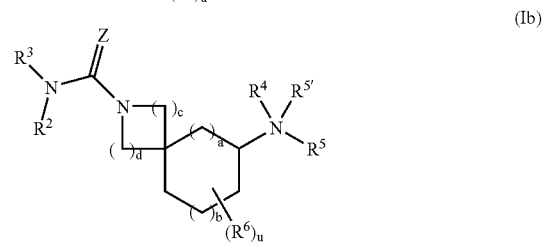

(Ib)

or pharmaceutically acceptable salt forms thereof, wherein Z, $R^1$, $R^2$, $R^3$, $R^4$, $R^5$, $R^{5'}$, $R^6$, a, b, c, d, and u are as defined herein in the specification. In addition, methods of treating and preventing inflammatory diseases such as asthma and allergic diseases, as well as autoimmune pathologies such as rheumatoid arthritis and atherosclerosis using modulators of formula (Ia) and (Ib) are disclosed.

11 Claims, No Drawings

OTHER PUBLICATIONS

Baba, et al "A small-molecule, nonpeptide CCR5 antagonist with highly potent and selective anti-HIV-1 activity", Proc. Natl. Acad. Sci, vol. 96, pp. 5698-5703 (1999).

Luster, M.D., Ph.D. Andrew D., "Chemokines-Chemotactic Cytokines that Mediate Inflammation", The New England Journal of Medicine, vol. 338, pp. 436-445, 2000.

Trivedi et al., "Chemokines: Targets for Novel Therapeutics", Ann. Reports Med. Chem., vol. 35, pp. 191-200 (2000).

Christoffers et al., "Regioselective Enamine Formation from Oxonia-Boranuida-Betaines and Their Application in Asymmetric Michael Reactions", Eur. J. Org. Chem., pp. 2845-2853 (2003).

* cited by examiner

SUBSTITUTED SPIRO AZABICYCLICS AS MODULATORS OF CHEMOKINE RECEPTOR ACTIVITY

This application claims the priority benefit of U.S. Provisional application No. 60/545,816 filed on Feb. 19, 2004, which is incorporated herein by reference in its entirety.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J. Med., 338, 436-445 (1998) and Rollins, Blood, 90, 909-928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell, 72, 415-425 (1993), Luster, New Eng. J. Med., 338, 436-445 (1998)); CCR-2 a and CCR-2B (or "CKR-2 a"/"CKR-2B" or "CC-CKR-2 a"/"CC-CKR-2B") [MCP-1, MCP-2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491-16494 (1995), Luster, New Eng. J. Med., 338, 436-445 (1998)); CCR-4 (or "CKR-4" or "CC-CKR-4") [TARC, MIP-1α, RANTES, MCP-1] (Power et al., J. Biol. Chem., 270, 19495-19500 (1995), Luster, New Eng. J. Med., 338, 436-445 (1998)); CCR-5 (or "CKR-5" OR "CC-CKR-5") [MIP-1α, RANTES, MIP-1β] (Sanson, et al., Biochemistry, 35, 3362-3367 (1996)); CCR-6 (or "CKR-6" or "CC-CKR-6") [LARC] (Baba et al., J. Biol. Chem., 272, 14893-14898 (1997)); CCR-7 (or "CKR-7" or "CC-CKR-7") [ELC] (Yoshie et al., J. Leukoc. Biol. 62, 634-644 (1997)); CCR-8 (or "CKR-8" or "CC-CKR-8") [1-309, TARC, MIP-1β] (Napolitano et al., J. Immunol., 157, 2759-2763 (1996), Bernardini et al., Eur. J. Immunol., 28, 582-588 (1998)); and CCR-10 (or "CKR-10" or "CC-CKR-10") [MCP-1, MCP-3] (Bonini et al, DNA and Cell Biol., 16, 1249-1256 (1997)).

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741-748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR3 expressing cells by HIV or in preventing the manipulation of immune cellular responses by viruses such as cytomegaloviruses.

SUMMARY OF THE INVENTION

Accordingly, the present invention provides novel agonists or antagonists of CCR-3, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating inflammatory diseases and allergic disorders comprising administering to a host in need of such treatment a therapeutically effective amount of at least one of the compounds of the present invention or a pharmaceutically acceptable salt or prodrug form thereof.

The present invention provides novel substituted spiro bicyclic amines, preferably urea-substituted spiro bicyclic amines, for use in therapy.

Further, the present invention provides the use of novel substituted spiro bicyclic amines, preferably urea-substituted spiro bicyclic amines, for the manufacture of a medicament for the treatment of allergic disorders.

These and other aspects, which will become apparent during the following detailed description, have been achieved by the inventors' discovery that compounds of formulas (Ia) and (Ib):

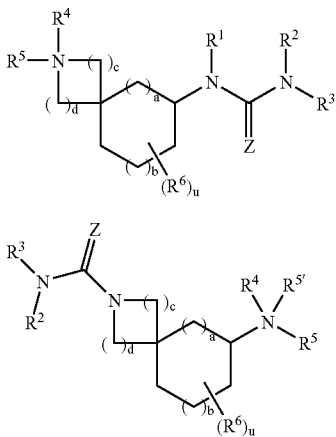

(Ia)

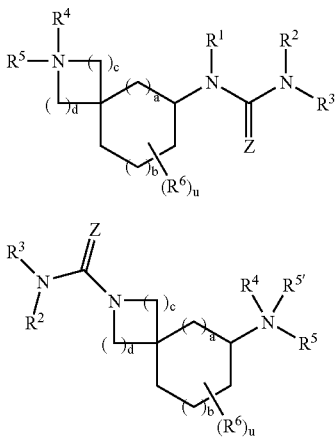

(Ib)

or stereoisomers or pharmaceutically acceptable salts thereof, wherein Z, $R^1$, $R^2$, $R^3$, $R^4$, $R^5$, $R^{5'}$ $R^6$, a, b, c, d, and u are defined below, and are effective modulators of chemokine activity.

DETAILED DESCRIPTION OF PREFERRED EMBODIMENTS

In one embodiment, the present invention discloses novel compounds of formulas (Ia) and (Ib):

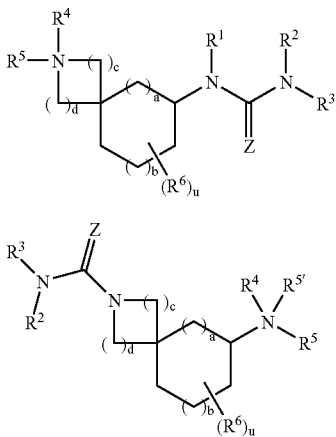

(Ia)

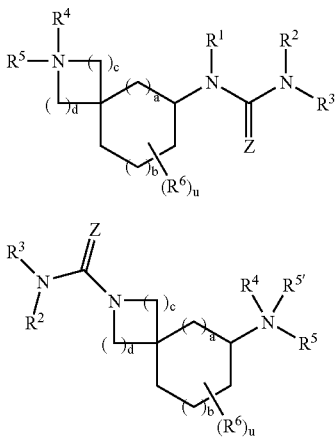

(Ib)

or stereoisomers or pharmaceutically acceptable salts thereof, wherein:

Z is selected from O, S, $N(R^d)$, $C(CN)_2$, $CH(NO_2)$, and $CH(CN)$;

$R^1$ and $R^2$ are independently selected from H, $C_{1-8}$ alkyl, $C_{2-8}$ alkenyl, and $C_{2-8}$ alkynyl;

$R^d$ is selected from H, $C_1$-$C_6$ alkyl, $C_3$-$C_6$ cycloalkyl, CON($R^f$)$R^f$, $OR^e$, CN, $NO_2$, and $(CH_2)_r$-phenyl substituted with 0-3 $R^{18}$;

$R^e$, at each occurrence, is independently selected from H, $C_{1-6}$ alkyl, $C_{3-6}$ cycloalkyl, and phenyl substituted with 0-3 $R^{18}$;

$R^f$, at each occurrence, is independently selected from H, $C_{1-6}$ alkyl, $C_{3-6}$ cycloaklyl, and phenyl substituted with 0-3 $R^{18}$, or optionally, two $R^f$s may be taken together with the nitrogen to which both are attached to form a pyrrolidine, piperidine, piperazine or morpholine ring;

$R^3$ is selected from a $(CR^{3'}R^{3'})_r$—$C_{3-10}$ carbocyclic residue substituted with 0-5 $R^{15}$ and a $(CR^{3'}R^{3'})_r$-5-10 membered heterocyclic system containing 1-4 heteroatoms selected from N, O, and S, substituted with 0-3 $R^{15}$;

$R^{3'}$, at each occurrence, is independently selected from H, $C_{1-6}$ alkyl, $(CH_2)_r C_{3-6}$ cycloalkyl, and phenyl;

$R^4$ is absent, taken with the nitrogen to which it is attached to form an N-oxide, or selected from $C_{1-8}$ alkyl, $C_{2-8}$ alkenyl, $C_{2-8}$ alkynyl, $(CH_2)_r C_{3-6}$ cycloalkyl, $(CH_2)_q C(O)R^{4b}$, $(CH_2)_q C(O)NR^{4a}R^{4a}$, $(CH_2)_q C(O)OR^{4b}$, and a $(CH_2)_r$—$C_{3-10}$ carbocyclic residue substituted with 0-3 $R^{4c}$;

$R^{4a}$, at each occurrence, is independently selected from H, $C_{1-6}$ alkyl, $(CH_2)_r C_{3-6}$ cycloalkyl, and phenyl;

$R^{4b}$, at each occurrence, is independently selected from $C_{1-6}$ alkyl, $C_{2-8}$ alkenyl, $(CH_2)_r C_{3-6}$ cycloalkyl, $C_{2-8}$ alkynyl, and phenyl;

$R^{4c}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, $(CH_2)_r OH$, $(CH_2)_r SC_{1-5}$ alkyl, $(CH_2)_r NR^{4a}R^{4a}$, and $(CH_2)_r$phenyl;

$R^5$ is selected from

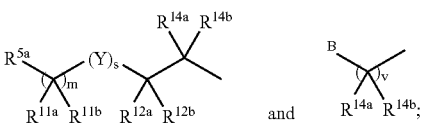

and

Y is selected from O, $N(R^{25})$, S, S(O), and $S(O)_2$;

ring B is a 5-7 membered cycloalkyl ring optionally containing a C=O, and being substituted with 0-2 $R^{11a}$, wherein the cycloalkyl ring is fused with a benzo group substituted with 0-3 $R^{16}$ or is fused with a 5-6 membered aromatic heterocyclic ring having 0-3 N, 0-1 O, or 0-1 S, the heterocyclic ring being substituted with 0-3 $R^{16}$;

alternatively, ring B is a 5-7 membered saturated heterocyclic ring containing 0-1 O, $N(R^{25})$, S, S(O), and $S(O)_2$, substituted with 0-2 $R^{11a}$, wherein the heterocyclic ring is fused with a benzo group substituted with 0-3 $R^{16}$ or is fused with a 5-6 membered aromatic heterocyclic ring having 0-3 N, 0-1 O, or 0-1 S, the heterocyclic ring being substituted with 0-3 $R^{16}$;

provided that if ring B is a heterocyclic ring, then the number of carbon atoms separating the heteroatom of ring B and the nitrogen atom of formula (Ia) or (Ib) bonded to $R^5$ is at least 2;

$R^{5'}$ is selected from H, $C_{1-8}$ alkyl, $C_{2-8}$ alkenyl, $C_{2-8}$ alkynyl, $(CH_2)_r C_{3-6}$ cycloalkyl, $(CH_2)_q C(O)R^{4b}$, $(CH_2)_q C(O)NR^{4a}R^{4a}$, $(CH_2)_q C(O)OR^{4b}$, and a $(CH_2)_r$—$C_{3-10}$ carbocyclic residue substituted with 0-3 $R^{4c}$;

alternatively, in formula (Ib), $R^5$ and $R^{5'}$ may together form a saturated ring containing 5 to 7 atoms optionally substituted with $C_{1-8}$ alkyl, $C_{2-8}$ alkenyl, $C_{2-8}$ alkynyl, $(CH_2)_r C_{3-6}$ cycloalkyl, $(CH_2)_q C(O)R^{4b}$, $(CH_2)_q C(O)NR^{4a}R^{4a}$, $(CH_2)_q C(O)OR^{4b}$, $(CH_2)_r$—$R^{5a}$, or O—$R^{5a}$;

$R^{5a}$ is selected from a $C_{3-10}$ carbocyclic residue substituted with 0-5 $R^{16}$, and a 5-10 membered heterocyclic residue containing 1-4 heteroatoms selected from N, O, and S, substituted with 0-3 $R^{16}$;

$R^6$, at each occurrence, is independently selected from $C_{1-6}$ alkyl, $C_{2-8}$ alkenyl, $C_{2-8}$ alkynyl, $(CH_2)_r C_{3-6}$ cycloalkyl, $(CF_2)_r CF_3$, CN, $(CH_2)_r NR^{6a}R^{6a}$, $(CH_2)_r OH$, $(CH_2)_r OR^{6b}$, $(CH_2)_r SH$, $(CH_2)_r SR^{6b}$, $(CH_2)_r C(O)OH$, $(CH_2)_r C(O)R^{6b}$, $(CH_2)_r C(O)NR^{6a}R^{6a}$, $(CH_2)_r NR^{6d}C(O)R^{6a}$, $(CH_2)_r C(O)$ $OR^{6b}$, $(CH_2)_rOC(O)R^{6b}$, $(CH_2)_rS(O)R^{6b}$, $(CH_2)_rS(O)_2R^{6b}$, $(CH_2)_rS(O)_2NR^{6a}R^{6a}$, $(CH_2)_rNR^{6d}S(O)_2R^{6b}$, and $(CH_2)_r$phenyl substituted with 0-3 $R^{6c}$;

with the proviso that if $R^6$ is attached to a carbon atom which also is attached to a nitrogen atom, or if two occurrences of $R^6$ are attached to the same carbon atom, then r contained within the definition of such $R^6$ must be greater than 0;

$R^{6a}$, at each occurrence, is independently selected from H, $C_{1-6}$ alkyl, $C_{3-6}$ cycloalkyl, and phenyl substituted with 0-3 $R^{6c}$;

$R^{6b}$, at each occurrence, is independently selected from $C_{1-6}$ alkyl, $C_{3-6}$ cycloalkyl, and phenyl substituted with 0-3 $R^{6c}$;

$R^{6c}$, at each occurrence, is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is independently selected from H, $C_{1-6}$ alkyl, and $C_{3-6}$ cycloalkyl;

$R^{11a}$ and $R^{12a}$, at each occurrence, are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)H$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, and $(CH_2)_r$phenyl substituted with 0-3 $R^{18}$;

with the proviso that if s is 1, then r contained within the definition of such $R^{11a}$ and $R^{12a}$ attached to carbon atoms bonded directly to Y must be greater than 0;

$R^{11b}$, $R^{12b}$, $R^{14a}$ and $R^{14b}$, at each occurrence, are independently selected from H, $C_{1-6}$ alkyl, $C_{2-8}$ alkenyl, $C_{2-8}$ alkynyl, $(CH_2)_qC_{3-6}$ cycloalkyl, $(CF_2)_rCF_3$, $(CH_2)_qN(R^{18a}YR^{18b}$, $(CH_2)_qOH$, $(CH_2)_qOR^{19}$, $(CH_2)_qSH$, $(CH_2)_qSR^{19}$, $(CH_2)_qC(O)OH$, $(CH_2)_qC(O)R^{19}$, $(CH_2)_qC(O)N(R^{18a})R^{18b}$, $(CH_2)_qN(R^{18c})C(O)R^{19}$, $(CH_2)_qC(O)OR^{19}$, $(CH_2)_qOC(O)R^{19}$, $(CH_2)_qS(O)R^{19}$, $(CH_2)_qS(O)_2R^{19}$, $(CH_2)_qS(O)_2N(R^{18a})R^{18b}$, $(CH_2)_qN(R^{18c})S(O)_2R^{19}$, and $(CH_2)_r$phenyl substituted with 0-3 $R^{18}$;

$R^{15}$, at each occurrence, is independently selected from $C_{1-8}$ alkyl, $(CH_2)_rC_{3-6}$ cycloalkyl, Cl, Br, I, F, $NO_2$, CN, $(CHR')_r$ $NR^{15a}R^{15a}$, $(CHR')_rOH$, $(CHR')_rO(CHR')_rR^{15d}$, $(CHR')_r$ SH, $(CHR')_rC(O)H$, $(CHR')_rS(CHR')_rR^{15d}$, $(CHR')_rC(O)OH$, $(CHR')_rC(O)(CHR')_rR^{15b}$, $(CHR')_rC(O)NR^{15a}R^{15a}$, $(CHR')_rNR^{15f}C(O)(CHR')_rR^{15b}$, $(CHR')_r$ $NR^{15f}C(O)NR^{15f}R^{15f}$, $(CHR')_rC(O)O(CHR')_rR^{15d}$, $(CHR')_rOC(O)(CHR')_rR^{15b}$, $(CHR')_rC(=NR^{15f})$ $NR^{15a}R^{15a}$, $(CHR')_r$ $NHC(=NR^{15f})NR^{15f}R^{15f}$, $(CHR')_rS$ $(O)(CHR')_rR^{15b}$, $(CHR')_rS(O)_2(CHR')_rR^{15b}$, $(CHR')_rS$ $(O)_2$ $NR^{15a}R^{15a}$, $(CHR')_rNR^{15f}S(O)_2(CHR')_rR^{15b}$, $C_{1-6}$ haloalkyl, $C_{2-8}$ alkenyl substituted with 0-3 R', $C_{2-8}$ alkynyl substituted with 0-3 R', $(CHR')_r$phenyl substituted with 0-3 $R^{15e}$, and a $(CH_2)_r$-5-10 membered heterocyclic system containing 1-4 heteroatoms selected from N, O, and S, substituted with 0-2 $R^{15e}$;

R', at each occurrence, is independently selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{15e}$;

$R^{15a}$, at each occurrence, is independently selected from H, $C_{1-6}$ alkyl, $C_{2-8}$ alkenyl, $C_{2-8}$ alkynyl, a $(CH_2)_r$—$C_{3-10}$ carbocyclic residue substituted with 0-5 $R^{15e}$, and a $(CH_2)_r$-5-10 membered heterocyclic system containing 1-4 heteroatoms selected from N, O, and S, substituted with 0-2 $R^{15e}$;

$R^{15b}$, at each occurrence, is independently selected from $C_{1-6}$ alkyl, $C_{2-8}$ alkenyl, $C_{2-8}$ alkynyl, a $(CH_2)_r$—$C_{3-6}$ carbocyclic residue substituted with 0-3 $R^{15e}$, and a $(CH_2)_r$-5-6 membered heterocyclic system containing 1-4 heteroatoms selected from N, O, and S, substituted with 0-2 $R^{15e}$;

$R^{15d}$, at each occurrence, is independently selected from $C_{2-8}$ alkenyl, $C_{2-8}$ alkynyl, $C_{1-6}$ alkyl substituted with 0-3 $R^{15e}$, a $(CH_2)_r$—$C_{3-10}$ carbocyclic residue substituted with 0-3 $R^{15e}$, and a $(CH_2)_r$-5-6 membered heterocyclic system containing 1-4 heteroatoms selected from N, O, and S, substituted with 0-3 $R^{15e}$;

$R^{15e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15f}$, and $(CH_2)_r$phenyl;

$R^{15f}$, at each occurrence, is independently selected from H, $C_{1-6}$ alkyl, $C_{3-6}$ cycloalkyl, and phenyl;

$R^{16}$, at each occurrence, is independently selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a}$, $(CHR')_rOH$, $(CHR')_rO(CHR')_rR^{16d}$, $(CHR')_rSH$, $(CHR')_rC(O)H$, $(CHR')_rS(CHR')_rR^{16d}$, $(CHR')_rC(O)OH$, $(CHR')_rC(O)(CHR')_rR^{16b}$, $(CHR')_rC(O)NR^{16a}R^{16a}$, $(CHR')_rNR^{16f}C(O)(CHR')_rR^{16b}$, $(CHR')_rC(O)O(CHR')_rR^{16d}$, $(CHR')_rOC(O)(CHR')_rR^{16b}$, $(CHR')_rC(=NR^{16f})NR^{16a}R^{16a}$, $(CHR')_rNHC(=NR^{16f})NR^{16f}R^{16f}$, $(CHR')_rS(O)(CHR')_rR^{16b}$, $(CHR')_rS(O)_2(CHR')_rR^{16b}$, $(CHR')_rS(O)_2NR^{16a}R^{16a}$, $(CHR')_rNR^{16f}S(O)_2(CHR')_rR^{16b}$, $C_{1-6}$ haloalkyl, $C_{2-8}$ alkenyl substituted with 0-3 R', $C_{2-8}$ alkynyl substituted with 0-3 R', and $(CHR')_r$phenyl substituted with 0-3 $R^{16e}$;

$R^{16a}$, at each occurrence, is independently selected from H, $C_{1-6}$ alkyl, $C_{2-8}$ alkenyl, $C_{2-8}$ alkynyl, a $(CH_2)_r$—$C_{3-10}$ carbocyclic residue substituted with 0-5 $R^{16e}$, and a $(CH_2)_r$-5-10 membered heterocyclic system containing 1-4 heteroatoms selected from N, O, and S, substituted with 0-2 $R^{16e}$;

$R^{16b}$, at each occurrence, is independently selected from $C_{1-6}$ alkyl, $C_{2-8}$ alkenyl, $C_{2-8}$ alkynyl, a $(CH_2)_r$-$C_{3-6}$ carbocyclic residue substituted with 0-3 $R^{16e}$, and a $(CH_2)_r$-5-6 membered heterocyclic system containing 1-4 heteroatoms selected from N, O, and S, substituted with 0-2 $R^{16e}$;

$R^{16d}$, at each occurrence, is independently selected from $C_{2-8}$ alkenyl, $C_{2-8}$ alkynyl, $C_{1-6}$ alkyl substituted with 0-3 $R^{16e}$, a $(CH_2)_r$—$C_{3-10}$ carbocyclic residue substituted with 0-3 $R^{16e}$, and a $(CH_2)_r$-5-6 membered heterocyclic system containing 1-4 heteroatoms selected from N, O, and S, substituted with 0-3 $R^{16e}$;

$R^{16e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$phenyl;

$R^{16f}$, at each occurrence, is independently selected from H, $C_{1-5}$ alkyl, and $C_{3-6}$ cycloalkyl, and phenyl;

$R^{18}$ at each occurrence, is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rS(O)C_{1-5}$ alkyl, $(CH_2)_rS(O)_2C_{1-5}$ alkyl, $(CH_2)_rS(O)_2N(R^{18a})R^{18b}$, $(CH_2)_rN(R^{18c})C(O)C_{1-5}$ alkyl $(CH_2)_rN(R^{18c})S(O)_2C_{1-5}$ alkyl, $(CH_2)_rC(O)N(R^{18a})R^{18b}$, $(CH_2)_rC(O)OC_{1-5}$ alkyl, $(CH_2)_rC(O)C_{1-5}$ alkyl, and $(CH_2)_rN(R^{18a})R^{18b}$;

$R^{18a}$, $R^{18b}$, and $R^{18c}$, at each occurrence, are independently selected from H, $C_{1-6}$ alkyl, and $C_{3-6}$ cycloalkyl;

alternatively, $R^{18a}$ and $R^{18b}$ along with the nitrogen to which both are attached form a pyrrolidine, piperidine, piperazine or morpholine ring;

$R^{19}$, at each occurrence, is independently selected from $C_{1-6}$ alkyl, $C_{3-6}$ cycloalkyl, and phenyl substituted with 0-3 $R^{18}$;

$R^{25}$, at each occurrence, is independently selected from H, $C_{1-6}$ alkyl, $C_{2-8}$ alkenyl, $C_{2-8}$ alkynyl, $(CH_2)_rC_{3-6}$ cycloalkyl, $(CH_2)_rC(O)R^{19}$, $(CH_2)_rC(O)N(R^{18a})R^{18b}$, $(CH_2)_rC(O)OR^{19}$, $(CH_2)_rS(O)_2R^{19}$, $(CH_2)_rS(O)_2N(R^{18a})R^{18b}$, and $(CH_2)_r$phenyl substituted with 0-3 $R^{18}$;

a is selected from 0 and 1;
b is selected from 0, 1, 2 and 3;
with the proviso that a+b is selected from 1, 2 and 3;
c is selected from 0 and 1;
d is selected from 1, 2 and 3;
with the proviso that c+d is selected from 2 and 3;
m is selected from 0, 1, and 2;
s is selected from 0 and 1;
with the proviso: m+s is selected from 0, 1, and 2;
v is selected from 0, 1, 2, and 3;
with the proviso: that the number of atoms in the shortest path linking the nitrogen to which $R^5$ is attached and the fused benzo or aromatic heterocyclic ring of B contained within such $R^5$ is less than or equal to 4;
r is selected from 0, 1, 2, 3, 4, and 5;
t is selected from 0, 1, 2, 3, 4, and 5;
q is selected from 1, 2, 3, 4, and 5; and
u is selected from 0, 1 and, 2.

Some preferred compounds are those compounds in which $R^1$ and $R^2$ are independently selected from H and $C_{1-8}$ alkyl;

$R^4$ is absent, taken with the nitrogen to which it is attached to form an N-oxide, or selected from $C_{1-8}$ alkyl, $(CH_2)_rC_{3-6}$ cycloalkyl, and a $(CH_2)_r$—$C_{3-10}$ carbocyclic residue substituted with 0-3 $R^{4c}$; and $R^{4c}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a}$, and $(CH_2)_r$phenyl.

Some particularly preferred compounds are those in which
Z is selected from O and S;

$R^6$, at each occurrence, is independently selected from $C_{1-4}$ alkyl, $(CH_2)_rC_{3-6}$ cycloalkyl, $(CH_2)_qNR^{6a}R^{6a}$, $(CH_2)_qOH$, $(CH_2)_qOR^{6b}$, $(CH_2)_rC(O)OH$, $(CH_2)_rC(O)R^{6b}$, $(CH_2)_rC(O)NR^{6a}R^{6a}$, $(CH_2)_qNR^{6d}C(O)R^{6a}$, $(CH_2)_rS(O)_2NR^{6a}R^{6a}$, $(CH_2)_rNR^{6d}S(O)_2R^{6b}$, and $(CH_2)_r$phenyl substituted with 0-3 $R^{6c}$;

$R^{6a}$, at each occurrence, is selected from H, methyl, ethyl, propyl, i-propyl, butyl, cyclopropyl, cyclopentyl, cyclohexyl, and phenyl;

$R^{6b}$, at each occurrence, is independently selected from methyl, ethyl, propyl, i-propyl, butyl, cyclopropyl, cyclopentyl, cyclohexyl, and phenyl;

$R^{6c}$, at each occurrence, is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$; and $R^{6d}$, at each occurrence, is independently selected from H, methyl, ethyl, propyl, i-propyl, butyl, cyclopropyl, cyclopentyl, and cyclohexyl.

Some more particularly preferred compounds are those in which $R^3$ is selected from a $(CR^{3'}H)_r$—$C_{3-8}$ carbocyclic residue substituted with 0-5 $R^{15}$, wherein the carbocyclic residue is selected from phenyl and naphthyl; and a $(CR^{3'}H)_r$-heterocyclic system substituted with 0-3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, indazolyl, isoindolyl, isothiadiazolyl, isoxazolyl, piperidinyl, pyrazolyl, 1,2,4-triazolyl, 1,2,3-triazolyl, tetrazolyl, thiadiazolyl, thiazolyl, oxazolyl, pyrazinyl, and pyrimidinyl; and $R^{5a}$ is selected from phenyl substituted with 0-5 $R^{16}$; and a heterocyclic residue substituted with 0-3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrazolyl, 1,2,4-triazolyl, 1,2,3-triazolyl, tetrazolyl, thiadiazolyl, thiazolyl, oxazolyl, pyrazinyl, and pyrimidinyl.

Some yet even more particularly preferred compounds are those in which
$R^1$ and $R^2$ are H;
$R^{5a}$ is phenyl substituted with 1-3 $R^{16}$;

$R^{16}$, at each occurrence, is independently selected from $C_{1-8}$ alkyl, $(CH_2)_rC_{3-6}$ cycloalkyl, $CF_3$, Cl, Br, I, F, $NR^{16a}R^{16a}$, $NO_2$, CN, OH, $OR^{16d}$, $C(O)R^{16b}$, $C(O)NR^{16a}R^{16a}$, and $NR^{16f}C(O)R^{16b}$;

$R^{6a}$, at each occurrence, is independently selected from H, methyl, ethyl, propyl, i-propyl, butyl, cyclopropyl, cyclopentyl, cyclohexyl, and $(CH_2)_r$phenyl substituted with 0-3 $R^{16e}$;

$R^{16b}$, at each occurrence, is independently selected from methyl, ethyl, propyl, i-propyl, butyl, cyclopropyl, cyclopentyl, cyclohexyl, and $(CH_2)_r$phenyl substituted with 0-3 $R^{16e}$;

$R^{16d}$, at each occurrence, is independently selected from methyl, ethyl, propyl, i-propyl, butyl, and phenyl;

$R^{16e}$, at each occurrence, is independently selected from methyl, ethyl, propyl, i-propyl, butyl, Cl, F, Br, I, CN, $NO_2$, $(CF_2)_rCF_3$, OH, and $(CH_2)_rOC_{1-5}$ alkyl; and $R^{16f}$, at each occurrence, is independently selected from H, methyl, ethyl, propyl, i-propyl, and butyl.

Additional preferred compounds are those compounds in which the compound is a compound of formula (Ia)

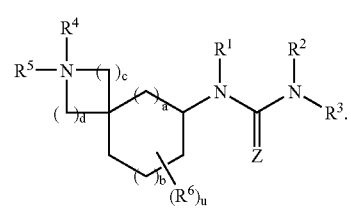

(Ia)

Additional particularly preferred compounds are those in which
$R^4$ is absent;
$R^5$ is

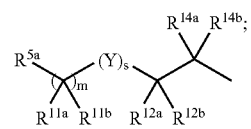

$R^{11a}$ and $R^{12a}$, at each occurrence, are independently selected from H, methyl, ethyl, propyl, i-propyl, butyl, pentyl, hexyl, cyclopropyl, cyclopentyl, cylohexyl, $CF_3$, $(CH_2)_rN(R^{18a})R^{18b}$, $(CH_2)_rOH$;

$R^{11b}$, $R^{12b}$, $R^{14a}$ and $R^{14b}$, at each occurrence, are independently selected from H, methyl, ethyl, propyl, i-propyl, butyl, pentyl, hexyl, cyclopropyl, cyclopentyl, cylohexyl, $CF_3$, $(CH_2)_qN(R^{18a})R^{18b}$, $(CH_2)_qOH$;

$R^{25}$, at each occurrence, is independently selected from H, methyl, ethyl, propyl, i-propyl, butyl, cyclopropyl, cyclopentyl, cyclohexyl, $(CH_2)_rC(O)R^{19}$, $(CH_2)_rC(O)N(R^{18a})R^{18b}$, $(CH_2)_rC(O)OR^{19}$, and $(CH_2)_r$phenyl substituted with 0-3 $R^{18}$.

Additional more particularly preferred compounds are those in which
$R^5$ is

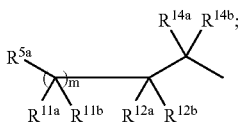

$R^{11a}$ and $R^{12a}$, at each occurrence, are independently selected from H, methyl, ethyl and OH;

$R^{11b}$, $R^{12b}$, $R^{14a}$, and $R^{14}$b, at each occurrence, are independently selected from H, methyl, and ethyl; and $R^{16}$, at each occurrence, is independently selected from methyl, Cl, F, $CF_3$, and CN.

Additional yet even more particularly preferred compounds are those in which $R^5$ is

Additional still yet even more particularly preferred compounds are those in which the compound is selected from the compounds of Tables 1 and 2.

In another embodiment, the present invention relates to pharmaceutical compositions, comprising a pharmaceutically acceptable carrier and a therapeutically effective amount of a compound of the present invention.

In another embodiment, the present invention relates to a method for modulation of chemokine receptor activity comprising administering to a patient in need thereof a therapeutically effective amount of a compound of the present invention.

In another embodiment, the present invention provides a method for treating or preventing asthma, comprising administering to a patient in need thereof a therapeutically effective amount of a compound of the present invention.

In another embodiment, the modulation of chemokine receptor activity comprises contacting a CCR3 receptor with an effective inhibitory amount of a compound of the present invention.

In another embodiment, the present invention provides a method for treating or preventing inflammatory disorders comprising administering to a patient in need thereof a therapeutically effective amount of a compound of the present invention, or a pharmaceutically acceptable salt thereof.

In another embodiment, the present invention provides a method for treating or preventing disorders selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma, preferably asthma, allergic rhinitis, atopic dermatitis, and inflammatory bowel diseases, more preferably asthma.

In another embodiment, the present invention provides a pharmaceutical composition comprised of a pharmaceutical composition of the present invention and one or more active ingredients.

In another embodiment, the present invention provides a method for treating inflammatory disorders comprising administering to a patient in need thereof a therapeutically effective amount of a pharmaceutical composition of the present invention and one or more active ingredients.

It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. C is and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom or ring is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $-C_vF_w$ where v=1 to 3 and w=1 to (2v+1)).

As used herein, the term "5-6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4 aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4 aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. Heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

The compounds herein described may have asymmetric centers. While all enantiomers/diasteriomers are intended to be covered by the instant application, one enantiomer of a compound of Formulas (Ia) and/or (Ib) may display superior biological activity over the opposite enantiomer. When required, separation of the racemic material can be achieved by methods known in the art. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. Only stable compounds are envisioned for this invention.

"Therapeutically effective amount" is intended to include an amount of a compound of the present invention alone or an amount of the combination of compounds claimed or an amount of a compound of the present invention in combination with other active ingredients effective to treat the inflammatory diseases described herein.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

Synthesis

The compounds of Formula Ia and Formula Ib can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. It will sometimes be desirable or necessary to modify the order of the synthetic steps or to select one particular process over another in order to obtain a desired compound of the invention, and such modifications will be recognized by those skilled in the art. It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is T. W. Greene and P. G. M. Wuts, *Protective Groups In Organic Synthesis,* Wiley and Sons, 1999. Some protecting groups are also discussed in M. Bodanszky and A. Bodanszky, *The Practice of Peptide Synthesis,* 2nd ed., Springer-Verlag, 1994; and M. Bodanszky, *Peptide Chemistry,* 2nd ed., Springer-Verlag, 1993.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula Ia into another compound of formula Ia, or one compound of formula Ib into another compound of formula Ib. Examples of such manipulations are conversion of an ester or a ketone to an alcohol; conversion of an ester to a ketone; interconversions of esters, acids, and amides; alkylation, acylation, and sulfonylation of alcohols and amines; and many others. Substituents can also be added using common reactions such as alkylation, acylation, halogenation, or oxidation. Such manipulations are well known in the art, and many reference works summarize procedures and methods for such manipulations. Some reference works which give examples and references to the primary literature of organic synthesis for many functional group manipulations as well as other transformations commonly used in the art of organic synthesis are R. C. Larock, *Comprehensive Organic Transformations,* VCH, 1989; A. Katritzky et al. (series editors), *Comprehensive Organic Functional Group Transformations,* Pergamon, 1995; and B. Trost and I. Fleming (series editors), *Comprehensive Organic Synthesis,* Pergamon, 1991.

Generally, compounds of Formula Ia can be synthesized by the routes described in Schemes 1, 2, or 3. In all schemes, P and P' are suitable protecting groups such as those described in T. W. Greene and P. G. M. Wuts, *Protective Groups In Organic Synthesis,* John Wiley and Sons, 1999; M. Bodanszky and A. Bodanszky, *The Practice of Peptide Synthesis,* 2nd ed., Springer-Verlag, 1994; or M. Bodanszky, *Peptide Chemistry,* 2nd ed., Springer-Verlag, 1993.

In Scheme 1, an appropriately substituted protected bicyclic amine 1 can be alkylated by reaction with an appropriate alkyl halide (X=Cl, Br, I) or activated alkyl alcohol (for example, X=methanesulfonate, p-toluenesulfonate, trifluoromethanesulfonate, or other leaving group capable of reacting with a nucleophilic amine) 2 to provide the protected bicyclic amine 3. The alkylation reaction can be performed with or without the addition of an acid scavenger or base such as carbonate and bicarbonate salts, triethylamine, 1,8-diazabicyclo[5.4.0]undec-7-ene (DBU), diisopropylethylamine (Hünig's base), 4-(N,N-dimethylamino)pyridine (DMAP), and the like. If the alkylating agent 2 is not an alkyl iodide, then potassium iodide can be added to facilitate the alkylation reaction if the solvent and reactants are compatible with such an additive. The reaction can be performed in a suitable solvent such as an alcohol, acetonitrile, acetone, 2-butanone, N,N-dimethylformamide (DMF), N,N-dimethylacetamide, N-methylpyrrolidinone, or dimethyl sulfoxide (DMSO), among others, and can be performed at a temperature in the range of room temperature to the reflux temperature of the solvent. The amine protecting group P can subsequently be removed to provide the amine 4. Protecting groups include phthalimide which can be removed by treatment with hydrazine; tert-butyloxycarbonyl (Boc) or bis-Boc which can be removed by treatment with an appropriate acid such as trifluoroacetic acid or hydrochloric acid in a suitable solvent; benzyloxycarbonyl (carbobenzyloxy or Cbz) which can be removed by a variety of catalytic reduction methods familiar to one skilled in the art; benzyl, diphenylmethyl or triphenylmethyl (trityl) or substituted variants of these groups which can also be removed by reduction methods; 2,4-dimethylpyrrole (S. P. Breukelman et al., J. Chem. Soc. Perkin Trans. I, 1984, 2801); N-1,1,4,4-tetramethyldisilylazacyclopentane (STABASE) (S. Djuric, J. Venit and P. Magnus, Tetrahedron Lett. 1981, 22, 1787); and other protecting groups.

Reaction of the amine 4 with an isocyanate or isothiocyanate 5 (Z=O or S) or with a carbamoyl chloride 6 (X'=Cl), phenyl carbamate 6 (X'=phenoxy) or 2- or 4-nitrophenyl carbamate 6 (X'=2- or 4-nitrophenoxy), or their thiocarbonyl equivalents, yields urea or thiourea 7. Reaction of 4 with a chloroformate or chlorothioformate 8 (Z=O or S) such as 2- or 4-nitrophenyl chloroformate or phenyl chloroformate (X"=2- or 4-nitro or H) or their thiocarbonyl equivalents, followed by treatment of the intermediate 9 with an amine 10, also yields the corresponding urea or thiourea 7. Likewise, reaction of carbamate 9 (X"=H, or 2- or 4-nitro) with disubstituted amine 11 yields trisubstiuted urea or thiourea 12. Reaction of the amine 4 with an N,N-disubstituted carbamoyl chloride 13 (X'=Cl), phenyl carbamate 13 (X'=phenoxy) or 2- or 4-nitrophenyl carbamate 13 (X'=2- or 4-nitrophenoxy), or their thiocarbonyl equivalents, also provides the corresponding N,N-disubstituted urea or thiourea 12.

Amine 4 can also be reductively alkylated with an aldehyde 14 to yield 15 by conditions familiar to one skilled in the art such as those reported in A. F. Abdel-Magid et al., Tetrahedron Lett. 1990, 31, 5595. This secondary amine can subsequently be reacted as described for reactions of 4 with isocyanates or isothiocyanates or carbamoyl chlorides or carbamates to provide trisubstituted ureas 16 or with carbamoyl chlorides or carbamates to yield tetrasubstituted ureas 17.

Amine 4 can also be converted into an isocyanate, isothiocyanate, carbamoyl chloride or thiocarbamoyl chloride (these reactions are not shown in Scheme 1). Examples of methods for such conversions can be found in J. Nowakowski, J. Prakt. Chem. 196, 338, 667; H.-J. Knoelker et al., Angew. Chem. 1995, 107, 2746; J. S. Nowick et al., J. Org. Chem. 1996, 61, 3929; H. A. Staab and W. Benz, Angew. Chem. 1961, 73 (for isocyanates); L. Strekowski et al., J. Heterocyclic Chem. 1996, 33, 1685; P. Kutschy et al., Synlett 1997, 289 (for isothiocyanates); F. Hintze and D. Hoppe, Synthesis 1992, 1216 (for carbamoyl chlorides); and W. Ried, H. Hillenbrand and G. Oertel, Justus Liebigs Ann. Chem. 1954, 590 (for thiocarbamoyl chlorides). These isocyanates, isothiocyanates, carbamoyl chlorides or thiocarbamoyl chlorides can then be reacted with $R^2R^3NH$ to provide di- or trisubstituted ureas or thioureas 13. An additional urea forming reaction involves the reaction of carbonyldiimidazole (CDI; J. L. Romine et al., Synthesis 1994, 846) with 4, followed by reaction of the intermediate imidazolide with 10 or in the reversed sequence (reaction of 10 with CDI, followed by treatment of the intermediate with 4). Activation of imidazolide intermediates facilitates urea formation (R. A. Bailey et al., Tetrahedron Lett. 1998, 39, 6267). One can also use 15 and 11 with CDI.

The reactions leading to formation of the ureas or thioureas can be done in aprotic inert solvents such as tetrahydrofuran, toluene, N,N-dimethylformamide, and the like, at a temperature in the range of room temperature to the reflux temperature of the solvent, and can employ the use of an acid scavenger or base such as carbonate and bicarbonate salts, triethylamine, DBU, diisopropylethylamine, 4-(N,N-dimethylamino)pyridine, and the like.

Scheme 1

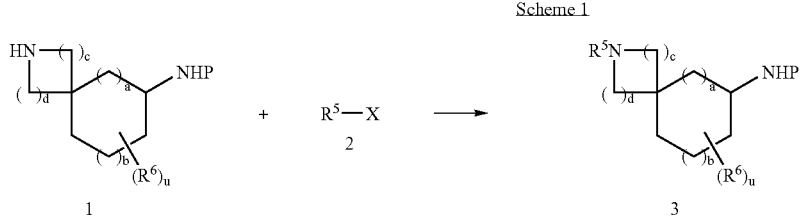

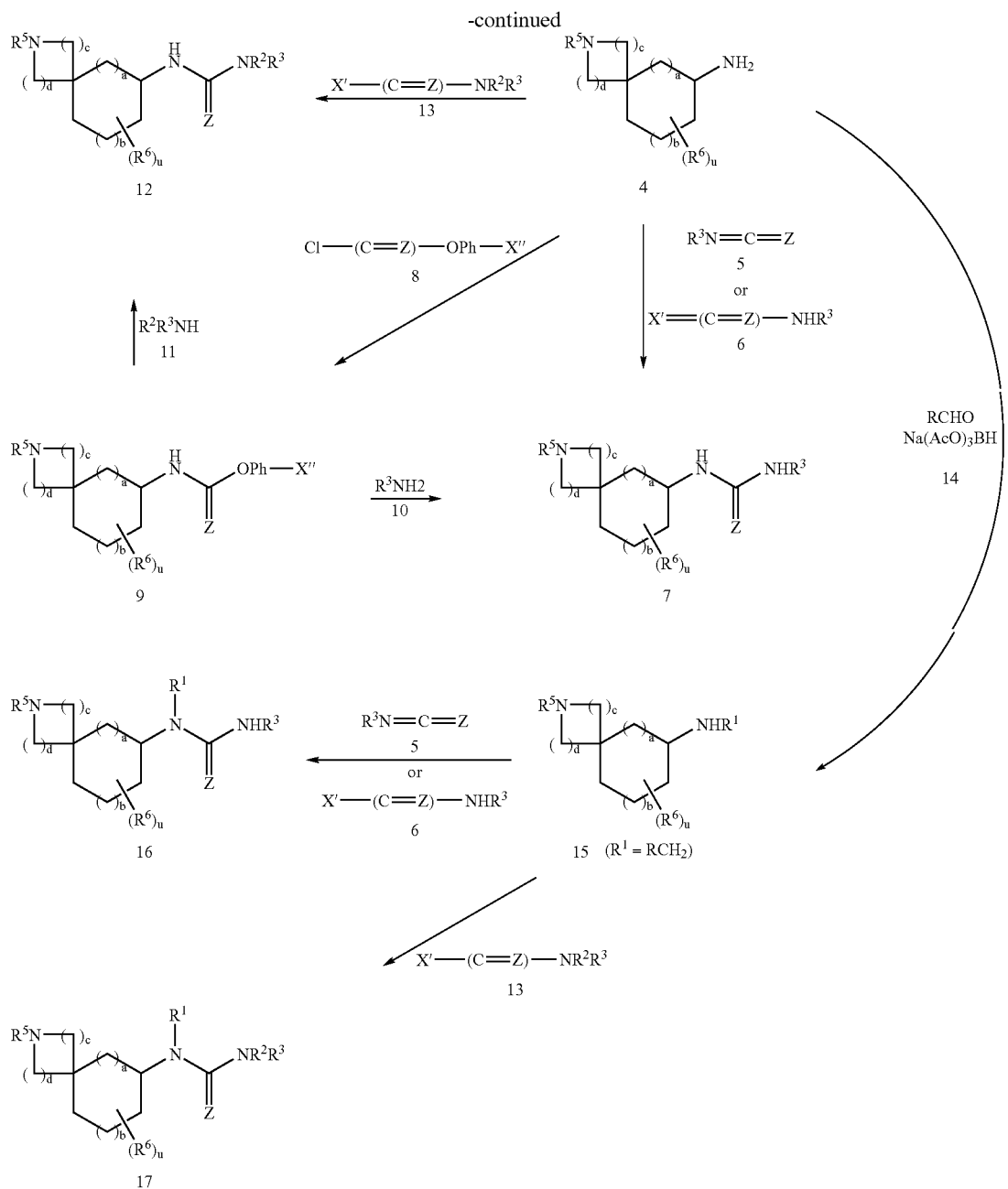

Scheme 2 describes alternative methods for attachment of certain selections of $R^5$. Reaction of amine 1 with an aldehyde 18 (R=H) or ketone 18 (R=$R^{14}$ a or $R^{13}$b in the compounds of Formula Ia, or R' and R' taken together form a ring as shown for certain selections of $R^5$ in the compounds of Formula Ia) in the presence of a reducing agent such as sodium triacetoxyborohydride, sodium cyanoborohydride, or a polymer-supported form of the cyanoborohydride anion, provides 19, where R'(R')CH is certain of the selections of $R^5$ in the compounds of Formula (Ia); that is, the point of attachment of $R^5$ to the ring nitrogen must bear at least one hydrogen. Such reductive alkylation of amines is well known in the art of organic synthesis, and can be achieved using reagents, solvents and reaction conditions described in, for example, R. O. Hutchins and M. K. Hutchins in B. N. Trost and I. Fleming, *Comprehensive Organic Chemistry*, Pergamon Press: New York, 1991, vol. 8; A. F. Abdel-Magid et al., J. Org. Chem. 1996, 61, 3849; or R. O. Hutchins et al., J. Chem. Soc. Chem. Commun. 1978, 1088. The protecting group of 19 can then be removed and the urea or thiourea can be prepared from the resulting amine 20 using the procedures outlined in Scheme 1.

Scheme 2 also demonstrates another method for the preparation of amines 19 where R'=H and RR'CH is certain of the selections of $R^5$ in the compounds of Formula (Ia); that is, point of attachment of $R^5$ to the piperidine nitrogen must bear two hydrogens. This method involves the acylation of amine 1 with a carboxylic acid 21 (X=OH) or the derived carboxylic acid chloride 21 (X=Cl) or a derived mixed anhydride 21 (X=OC(=O)OR", where R" is an alkyl group) to provide the amide 22. Such amide-forming reactions can be achieved using a wide variety of reagents and conditions known to one skilled in the art, such as for example the methods described in M. Bodanszky and A. Bodanszky, *The Practice of Peptide Synthesis,* 2nd ed., Springer-Verlag: New York, 1994; and M. Bodanszky, *Peptide Chemistry,* 2nd ed., Springer-Verlag: New York, 1993. Conversion of a carboxylic acid to the derived carboxylic acid chloride or mixed anhydride (21, X=Cl or OC(=O)OR') can be achieved using a variety of conditions and reagents well known to one skilled in the art, such as for example using thionyl chloride, phosphorus pentachloride, oxalyl chloride, or an alkyl chloroformate such as isobutyl chloroformate. (See, for example, the above-cited references by Bodanszky, as well as Ansell in S. Patai, *The Chemistry of Carboxylic Acids and Esters,* Wiley Interscience: New York, 1969, 35-68.)

The amide 22 can be converted to the amine 19 (R'=H) using a reducing agent such as borane or lithium aluminum hydride, a reaction well known to one skilled in the art. Such reductions can be carried out in a solvent such as a dialkyl ether or tetrahydrofuran, at a temperature in the range 0° C. to the boiling point of the solvent. The resulting amine 19 can then be deprotected to provide 20 (R'=H), which can be converted to the urea or thiourea using the procedures outlined in Scheme 1.

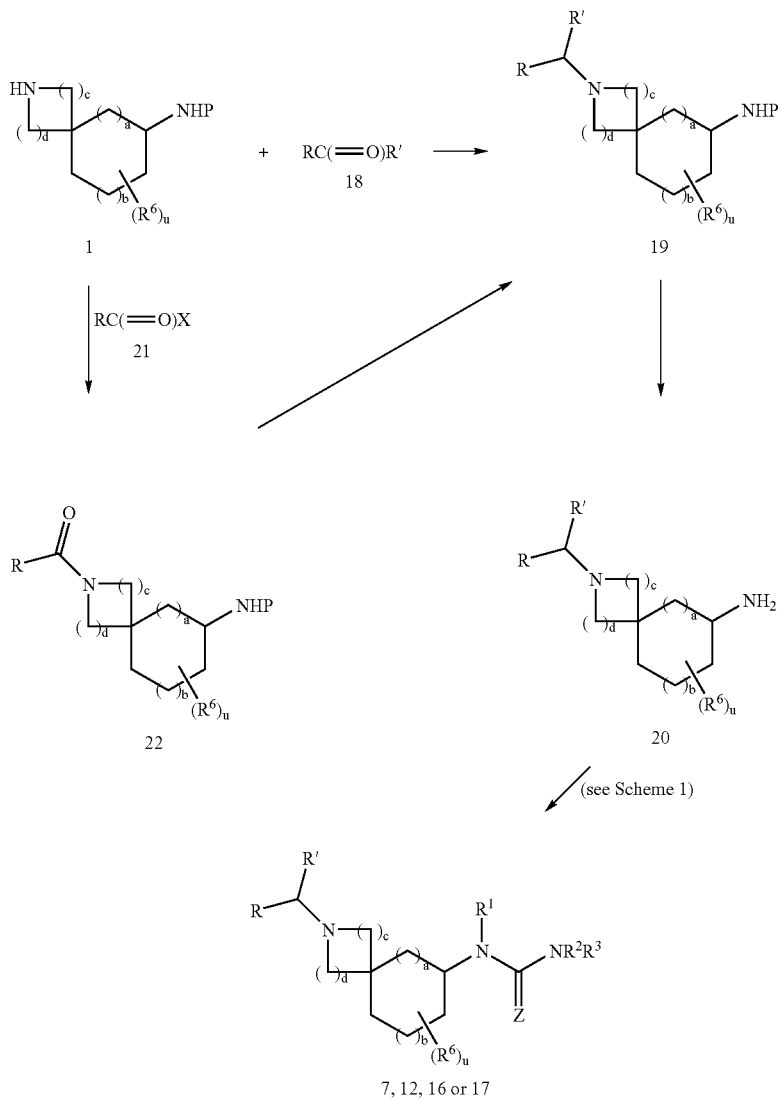

Scheme 2

Compounds of Formula (Ia) can also be prepared using the sequence of reactions shown in Scheme 3. A protected bicyclic diamine 23 can be converted to the urea or thiourea 24 using one of the methods depicted in Scheme 1 for the conversion of 4 to 7, 12, 16 or 17. The protecting group can be removed, and the resulting amine 25 can be alkylated using one of the methods depicted in Schemes 1 and 2 to provide the desired compound.

Scheme 3

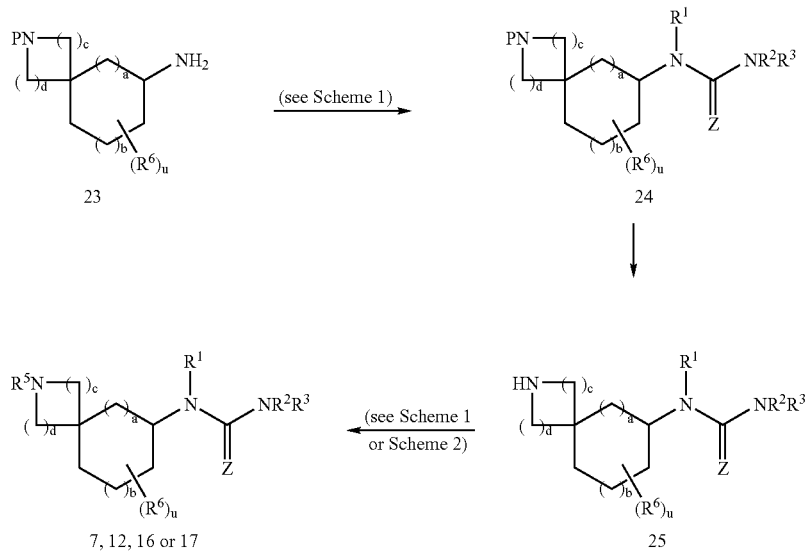

Guanidines of Formula Ia (Z=NR$^d$) can be synthesized by the methods outlined in Scheme 4. Compound 26 can be methylated to yield the methylisothiourea 27. Displacement of the thiomethyl group with amines can provide substituted guanidines 28 (as reported by H. King and I. M. Tonkin, J. Chem. Soc. 1946, 1063; and references cited therein). Alternatively, reaction of thiourea 26 with amines in the presence of triethanolamine and lac sulfur which facilitates the removal of hydrogen sulfide can provide substituted guanidines 28 (as reported by K. Ramadas, Tetrahedron Lett. 1996, 37, 5161 and references cited therein). The use of carbonimidoyldichloride 29 or 30 followed by sequential displacements by amines provides the corresponding substituted guanidine 28 (as reported by S. Nagarajan et al., Synth. Commun. 1992, 22, 1191, and references cited therein). In a similar manner, carbonimidoyldichlorides R$^2$—N=C(Cl)$_2$ and R$^3$—N=C(Cl)$_2$ (not shown in Scheme 4) can also be reacted sequentially with amines to yield di- and trisubstituted guanidine 28.

Scheme 4

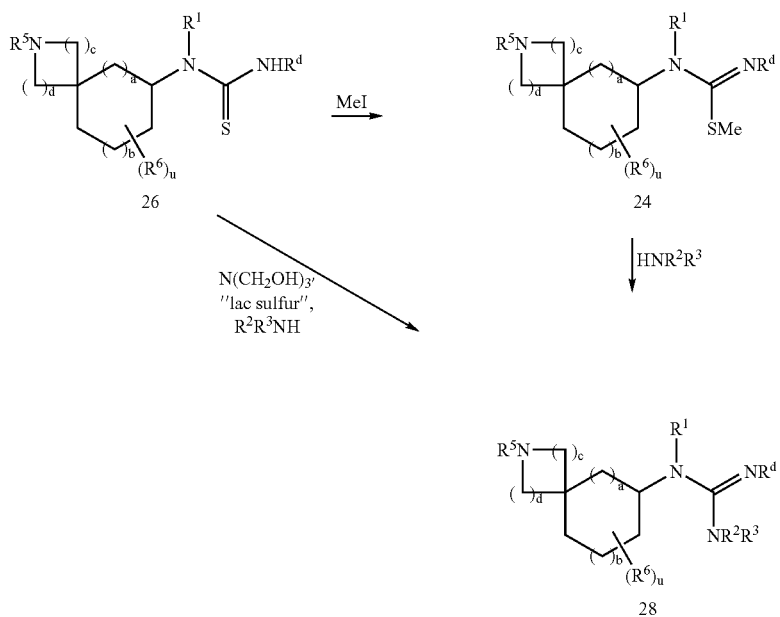

-continued

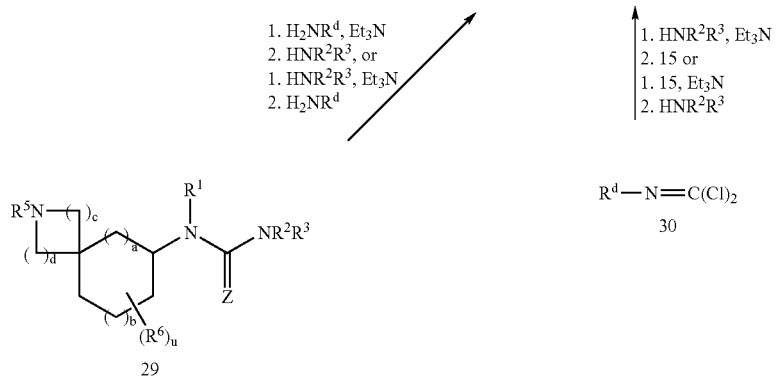

Compounds of Formula Ia where Z=N—CN, CHNO$_2$, and C(CN)$_2$ can be synthesized by the methods shown in Scheme 5. For example, following the method reported by P. Traxler et al., J. Med. Chem. 1997, 40, 3601, amine 31 can react with malononitrile 32 in an inert solvent or neat, at a temperature in the range of room temperature to the boiling point of the solvent, or at the melting point of the solid/solid mixture, to provide the malononitrile 33. This in turn can undergo reaction with amine 15 under similar conditions to those given above to give malononitrile 34. Likewise, a similar reaction sequence can be used to prepare 37 (see, for example, J. Hoffman et al., J. Med. Chem. 1983, 26, 140) and 40 (see, for example, K. Atwal, J. Med. Chem. 1998, 41, 271).

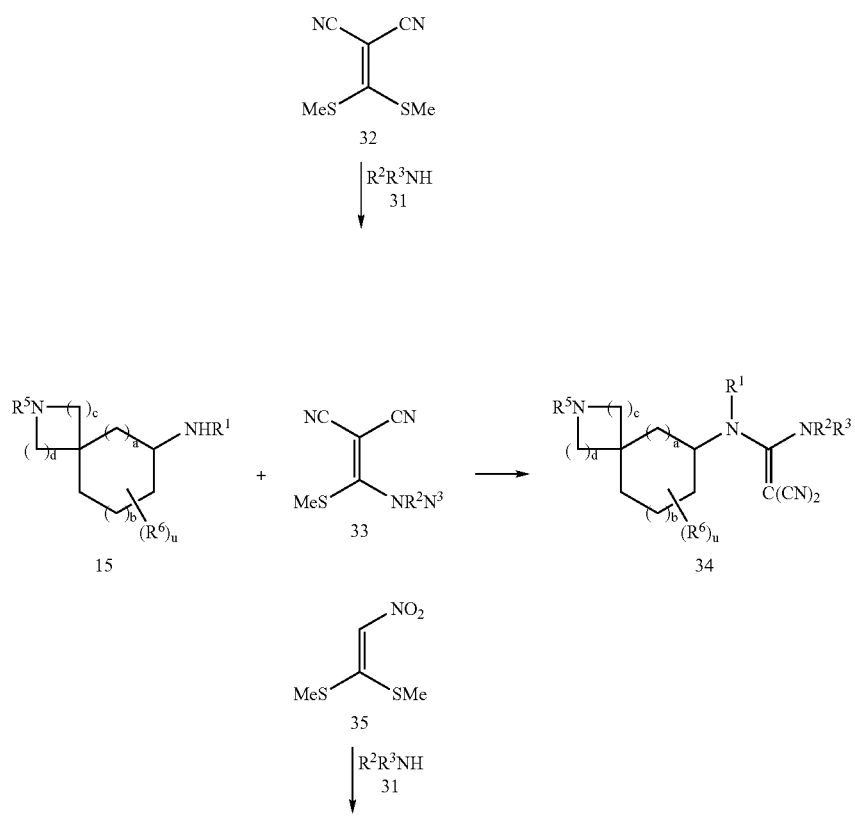

-continued

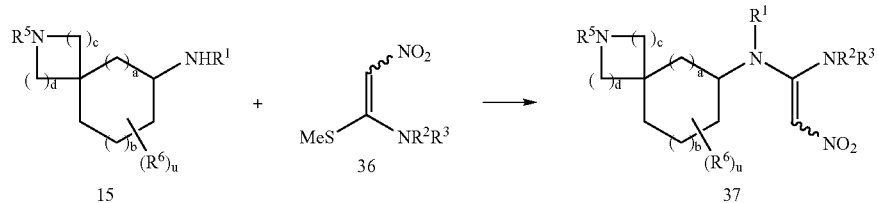

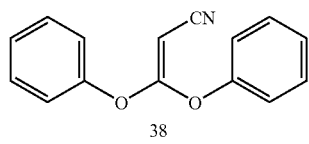

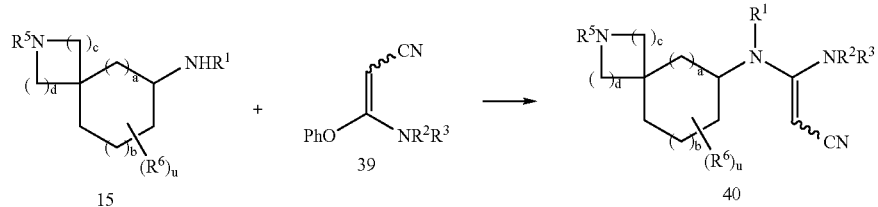

The synthetic methods illustrated in Schemes 1 through 5 can also be used to prepare compounds of Formula Ib. Examples of this are shown in Scheme 6. The protected bicyclic amine 41 can be alkylated with an aldehyde or ketone 18, as described for Scheme 2, to provide the substituted amine 42. This amine can optionally be alkylated again, using methods described for Schemes 1 and 2, to provide 43, where $R^5$ is equivalent to CH(R')R' of 42. (Alternatively, if desired, the secondary amine of 42 can be protected using a suitable protecting group.) Removal of the protecting group of 43 can provide the cyclic amine 44, which can be converted to the urea or related compound 45 using methods shown in Schemes 1, 4 or 5.

Another approach to compounds of Formula Ib, also shown in Scheme 6, involves reductive amination of the ketone 46 with an amine $NHR^5R^5$, using methods known in the literature as described for Schemes 1 and 2. The resulting amine 43 can then be converted to 45 by deprotection and conversion to the urea or related compound, as already described.

Scheme 6

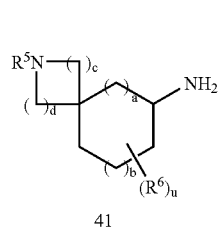

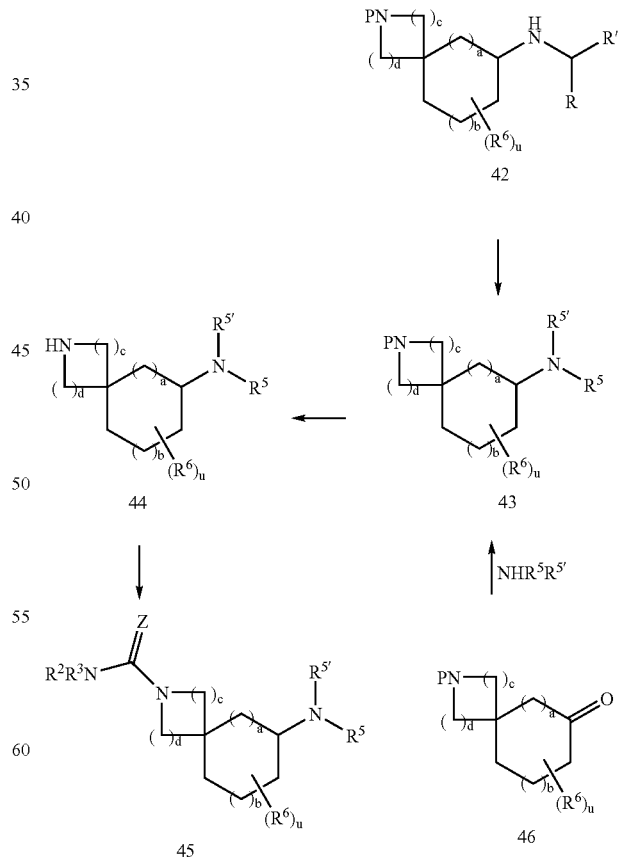

Many amines are commercially available and can be used as 10, 11, and the amines which are precursors to isocyanates or isothiocyanates 5 or carbamoyl chlorides, phenyl carbamates or 2- or 4-nitrophenylcarbamates 6 and 13, as well as other amines whose use is illustrated in Schemes 1 through 6. There are numerous methods for the synthesis of non-commercially available amines familiar to one skilled in the art. For example, aldehydes and ketones can be converted to their o-benzyl oximes and then reduced with lithium aluminum hydride to provide amines (S. Yamazaki et al., Bull. Chem. Soc. Japan 1986, 59, 525). Ketones and trifluoromethyl ketones undergo reductive amination in the presence of titanium (IV) chloride followed by sodium cyanoborohydride to yield amines (C. Barnet et al., Tetrahedron Lett. 1990, 31, 5547). Aldehydes and ketones undergo reductive amination with sodium triacetoxyborohydride and amines to yield other amines (A. Abdel-Magid et al., J. Org. Chem. 1996, 61, 3849). Aryl amines can be synthesized from aromatic and heterocyclic hydroxyl groups (for example, phenols) using the Smiles rearrangement (J. Weidner and N. Peet, J. Heterocyclic Chem. 1997, 34, 1857). Displacement of halides, p-toluenesulfonates, methanesulfonates, trifluoromethanesulfonates, and the like with azide or cyanide followed by reduction with lithium aluminum hydride or catalytic hydrogenation or other reduction methods yields amines. Sodium diformyl amide (H. Yinglin and H. Hongwen, Synthesis 1989, 122), potassium phthalimide and bis-Boc-amine anion can all displace halides and other leaving groups, followed by standard deprotection methods to yield amines. Other methods to synthesize more elaborate amines involve the Pictet-Spengler reaction, imine/immonium ion Diels-Alder reactions (S. Larsen and P. Grieco, J. Amer. Chem. Soc. 1985, 107, 1768; P. Grieco et al., J. Org. Chem. 1988, 53, 3658; J. Cabral and P. Laszlo, Tetrahedron Lett. 1989, 30, 7237), amide reduction for example with lithium aluminum hydride or borane, organometalic addition to imines (A. Bocoum et al., J. Chem. Soc. Chem. Commun. 1993, 1542), and others which are familiar to one skilled in the art. (Additional methods for amine preparation are described further in the discussion of Scheme 9 below.)

Various aromatic amines can be synthesized using the methods shown in Scheme 7. For example, nitrobenzeneboronic acids 47 can undergo Suzuki-type coupling reactions with a wide variety of substituted iodo-, bromo-, chloro-, or trifluoromethanesulfonyloxy-substituted arenes (arene representing phenyl, naphthyl, and the like), aromatic heterocycles, alkanes, alkenes, or alkynes 48 (X=I, Br, Cl, or $CF_3SO_3$; R=optionally substituted aryl, heteroaryl, alkyl, alkenyl, or alkynyl) (see, for example, A. Suzuki, Pure Appl. Chem. 1991, 63, 419; J. M. Fu and V. Snieckus, Tetrahedron Lett. 1990, 31, 1665; and M. Moreno-Manas et al., J. Org. Chem. 1995, 60, 2396) to provide 49. The above reactions can also undergo carbonyl insertion in the presence of an atmosphere of carbon monoxide (Ishiyama et al., Tetrahedron Lett. 1993, 34, 7595) to provide 51. Arylboronic acids 47 can also be coupled with amines 53 (R=alkyl, aryl, heteroalkyl; X'=NH), amides 53 (R'=alkylcarbonyl, arylcarbonyl, and the like; X'=N-alkyl or N-aryl), sulfonamides 53 (R'=alkylsulfonyl, arylsulfonyl and the like; X'=N-alkyl), phenols 53 (R'=aryl, X'=O) or NH-containing heteroarenes 53 (X'=N, with R representing the remainder of a heteroarene such as pyrazole, imidazole, triazole, indazole and the like) to provide the correspondng coupled products 54 (D. Chan et al., Tetrahedron Lett. 1998, 39, 2933; P. Lam et al., Tetrahedron Lett. 1998, 39, 2941; P. Lam et al., Synlett 2000, 674).

The resulting nitro-containing compounds of Scheme 6 (49, 51 and 54) can then be reduced to the corresponding amines 50, 52 and 55 either using catalytic hydrogenation, or using a number of chemical methods well known in the art, for example with tin (II) chloride, iron or tin with an acid, titanium (III) chloride, or ammonium sulfide. The carbonyl insertion compounds 51 and 52 can also undergo reduction of the carbonyl group to either CH(OH) or $CH_2$ linkages using methods well known in the art, for example with sodium borohydride or triethylsilane with trifluoroacetic acid.

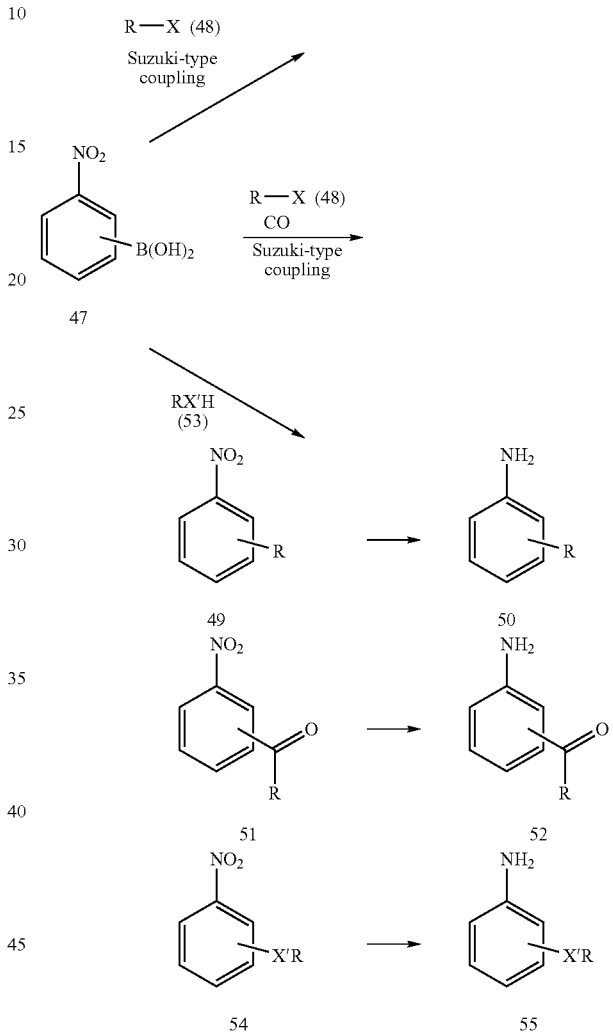

Scheme 7

Aromatic amines can also be prepared as shown in Scheme 8. Protected aminobromobenzenes or protected aminophenyl trifluoromethanesulfonates 56, or heterocyclic analogs of 56, can undergo Suzuki-type couplings with arylboronic acids or heteroarylboronic acids 57 (R'=aryl or heteroaryl). These same bromides or trifluoromethanesulfonates 56 can also undergo Stille-type couplings (A. Echavarren and J. Stille, J. Amer. Chem. Soc. 1987, 109, 5478) with aryl, alkenyl, or heteroaryl stannanes 58 (R'=aryl, heteroaryl, or alkenyl). Bromides or trifluoromethanesulfonates 56 can also undergo Negishi-type couplings (E. Negishi, Accts. Chem. Res. 1982, 15, 340; M. Sletzinger et al., Tetrahedron Lett. 1985, 26, 2951) with aryl, heteroaryl, alkyl or alkenyl zinc bromides or iodides 59 (R'=aryl, heteroaryl, alkyl or alkenyl; X'=Br or I). Bromides, chlorides or trifluoromethanesulfonates 56 can also undergo couplings with amines 62 (R=alkyl or aryl, X"=NH, N-alkyl, and the like), carbamates 62

(R=alkoxycarbonyl, X"=NH), alcohols 62 (R=alkyl, X"=O) or phenols 62 (R'=aryl, X"=O) to provide the corresponding amines, carbamates, or ethers 63 (see, for example, J. Hartwig, Angew. Chem. 1998, 37, 2046; J. Hartwig et al., J. Org. Chem. 1999, 64, 5575; J. Wolfe et al., J. Org. Chem. 2000, 65, 1158; and J. Wolfe and S. Buchwald, J. Org. Chem. 2000, 65, 1144). The protected amines 60 or 63 resulting from these various coupling reactions can be deprotected to provide amines 61 or 64, respectively.

aminophenol can provide benzimidazole 66 ($Y^1$=NH, $Y^2$ and $Y^3$ are carbon with a benzene ring fused to the $Y^2$—$Y^3$ bond) or benzoxazole 66 ($Y^1$=O, $Y^2$ and $Y^3$ are carbon with a benzene ring fused to the $Y^2$—$Y^3$ bond) (M. DeLuca and S. Kerwin, Tetrahedron 1997, 53, 457). Reaction of an acid chloride 65 (X=Cl) with an aziridine-2-carboxylic acid ester, followed by rearrangement of the amide and oxidation, can provide oxazole 66 ($Y^1$=O, $Y^2$=CH, $Y^3$=C—COO-alkyl) (F. Eastwood et al., J. Chem. Soc. Perkin Trans. 1 1997, 35). The

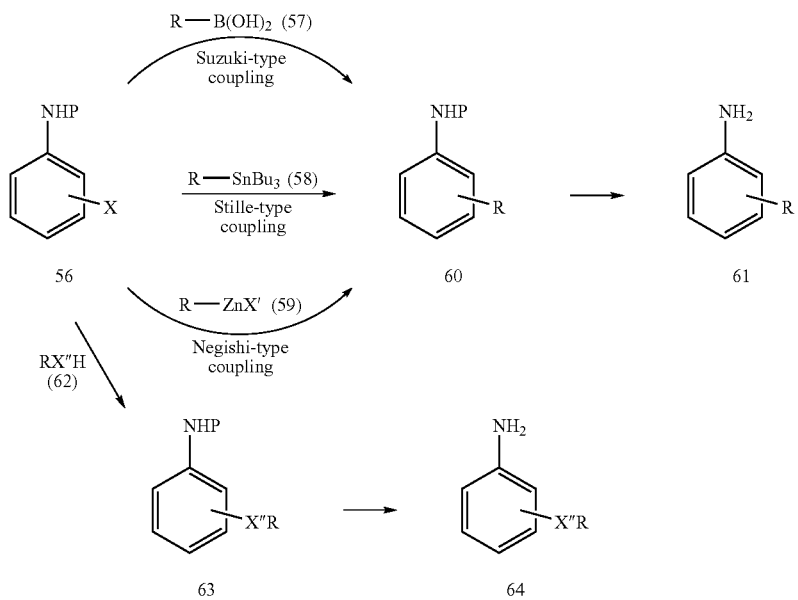

Scheme 8

Aromatic amines bearing certain heteroaryl substituents linked through a carbon atom can also be prepared as shown in Scheme 9. Benzoic acid derivatives 65 (X'=nitro or protected amine) can be reacted with a variety of reagents to prepare a variety of five-membered ring heteroaryl-substituted compounds 66. A few examples known in the literature are described, but are not to be considered limitations on the method shown in Scheme 9. Reaction of amide 65 (X=$NH_2$) with triazidochlorosilane can provide tetrazole 66 ($Y^1$=NH, $Y^2$ and $Y^3$=N) (A. El-Ahl et al., Tetrahedron Lett. 1997, 38, 1257). Reaction of amide 65 (X=NH-alkyl) with azidotrimethylsilane can provide tetrazole 66 ($Y^1$=N-alkyl, $Y^2$ and $Y^3$=N) (J. Duncia et al., J. Org. Chem. 1991, 56, 2395). Reaction of hydrazide 65 (X=$NHNH_2$) with an acylating agent, followed by dehydration, can provide oxadiazole 66 ($Y^1$=O, $Y^2$=C-alkyl or C-aryl, $Y^3$=N); further reaction of this oxadiazole with an amine can provide triazole 66 ($Y^1$=N-alkyl, $Y^2$=C-alkyl or C-aryl, $Y^3$=N) (P. Carlsen and K. Joergensen, J. Heterocyclic Chem. 1994, 31, 805). Reaction of an acid chloride 65 (X=Cl) with an imidate ester iminophosphorane derived from azidoacetonitrile can provide imidazole 66 ($Y^1$=NH, $Y^2$ and $Y^3$=CH or C-alkyl) (P. Molina et al., Synthesis 1995, 449). Reaction of a acylated glycine 65 (X=N(alkyl)$CH_2$COOH) with a carboxylic acid anhydride, followed by treatment with a guanidine or ammonium acetate, can provide imidazole 66 ($Y^1$=NH, $Y^2$=C-alkyl or C-aryl, $Y^3$=C-alkyl, C-aryl or CH) (M. Kawase et al., Heterocycles 1995, 41, 1617). Reaction of an acid or acid chloride 65 (X=OH or Cl) with an ortho-phenylenediamine or an orthothioamide corresponding to 65 (X=$NH_2$, with the carbonyl oxygen replaced by sulfur) can react with an alpha-bromoketone to provide thiazole 66 ($Y^1$=S, $Y^2$ and $Y^3$=CH, C-alkyl or C-aryl) (O. Uchikawa et al., Chem. Pharm. Bull. 1996, 44, 2070). Reaction of acid chloride 65 (X=Cl) with a beta-hydroxyamine, followed by treatment with phosphorus pentasulfide and oxidation, can also provide thiazole 66 ($Y^1$=S, $Y^2$ and $Y^3$ are CH, C-alkyl or C-aryl) (R'. Aitken et al., J. Chem. Soc. Perkin Trans. 1 1997, 935). The protected amines 66 (X'=NHP) or nitrobenzenes 66 (X'=$NO_2$) resulting from these various reactions and others like them can be deprotected or reduced, respectively, as described for Schemes 7 and 8, to provide amines 67.

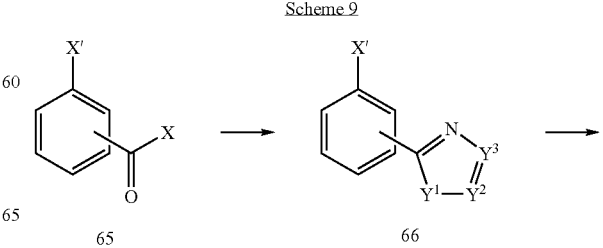

Scheme 9

-continued

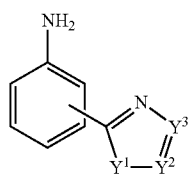
67

The amines described above (commercially available, or prepared as described in Schemes 7, 8 and 9, and other amines) can be converted to isocyanates 5 (Z=O) using methods such as those reported by J. Nowakowski, J. Prakt. Chem. 1996, 338, 667; H. J. Knoelker et al., Angew. Chem. 1995, 107, 2746; J. Nowick et al., J. Org. Chem. 1996, 61, 3929; and H. Staab and W. Benz, Angew. Chem. 1961, 73. They can also be converted to isothiocyanates 5 (Z=S) using methods such as those reported by L. Strekowski et al., J. Heterocyclic Chem. 1996, 33, 1685; and P. Kutschy et al., Synlett 1997, 289. They can also be converted (after optional reductive alkylation with an $R^2$ group) to carbamoyl chlorides 6 or 13 (X'=Cl, Z=O), for example, as reported by F. Hintze and D. Hoppe, Synthesis 1992, 1216; to thiocarbamoyl chlorides 6 or 13 (X'=Cl, Z=S), for example, as reported by W. Ried et al., Justus Liebigs Ann. Chem. 1954, 590; or to phenyl or 2- or 4-nitrophenylcarbamates 6 or 13 (X'=phenoxy, 2-nitrophenoxy or 4-nitrophenoxy; Z=O) by treatment with the corresponding phenyl, 2-nitrophenyl or 4-nitrophenyl chloroformate under suitable conditions known to one skilled in the art.

The bicyclic diamines and protected forms thereof (1 in Schemes 1 and 2, 23 in Scheme 3, and 41 in Scheme 6) can be prepared using a variety of methods, as described in Schemes 10 and 12. Compounds 4 and 15 of Scheme 1 and 20 of Scheme 3 can also be prepared by the methods in Schemes 10 and 12. If the ring nitrogen of any of these intermediates is protected with an amine protecting group, this protecting group can be removed at any step of the reaction sequences shown and replaced by a group $R^5$ of Formula Ia, using one of the alkylation methods described in Schemes 1, 2, or 3 or another method, as long as the deprotection and alkylation reactions are compatible with the structure of the intermediate upon which the reactions are performed, and as long as the resulting $R^5$-substituted intermediate is compatible with the remaining reactions in the sequence. Likewise, in some of the reaction sequences shown in Schemes 10 and 12, it may be possible to substitute a group $R^5$ of Formula Ia for the protecting group on the ring nitrogen, providing direct access to 4 or 20. Such cases will be apparent to one skilled in the art.

One method for the preparation of bicyclic diamines and suitably protected forms thereof (such as 1 in Schemes 1 and 2, 23 in Scheme 3, and 41 in Scheme 6), shown in Scheme 10, involves conversion of a carboxylic acid 68 (R'=OH) or carboxylic acid derivative such as an acid chloride 68 (R'=Cl) or mixed anhydride 68 (R'=OC(=O)alkyl or OC(=O)Oalkyl) into an acyl azide 69, followed by thermal rearrangement to the isocyanate 70, commonly referred to as the Curtius rearrangement. Treatment of the intermediate isocyanate with water can provide the amine 71 directly. Alternatively, treatment of the intermediate isocyanate with an alcohol such as benzyl alcohol can provide the carbamate 72, which can serve as a protected form of the amine 71 and either deprotected to provide 71 or used directly, for example, as described for Schemes 1 and 2. Alternatively, the isocyanate 70 can sometimes be isolated, in which case it can be treated with an amine to form a urea as discussed previously. Some examples of the use of the Curtius rearrangement to effect transformations analogous to those shown in Scheme 10 have been reported by J. Altman and D. Ben-Ishai, Tetrahedron Asymmetry 1994, 5,887; K. Ninomiya, T. Shioiri and S. Yamada, Tetrahedron 1974, 30, 2151; L. M. Gustavson and A. Srinivasan, Synth. Commun. 1991, 21, 265; R'. Pires and K. Burger, Synthesis 1996, 1277; and E. Neufellner, H. Kapeller and H. Griengl, Tetrahedron 1998, 54, 11043.

A related method for achieving the transformation of a carboxylic acid derivative to an amine as shown in Scheme 10 involves treatment of an amide 68 (R'=$NH_2$) with an oxidizing agent such as sodium hypobromite or I,I-bis-(trifluoroacetoxy)iodobenzene to provide the amine 71, a reaction commonly referred to as the Hofmann rearrangements. This transformation is reviewed by Wallis and Lane, Org. Reactions 1946, 3, 267; a more recent example was reported by Radhakrishna et al., J. Org. Chem. 1979, 44, 1746.

Scheme 10

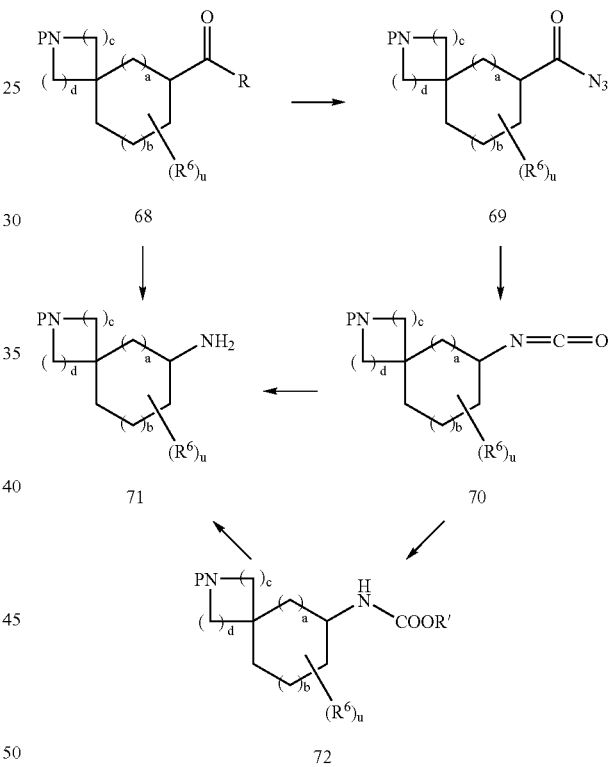

The carboxylic acids and derivatives 68 can be prepared using methods well known in the art of organic synthesis.

Another method for the preparation of bicyclic diamines and suitably protected forms thereof (such as 1 in Schemes 1 and 2, 23 in Scheme 3, and 41 in Scheme 6) is by conversion of a ketone such as 73 to the oxime or substituted oxime 74 (X'=OH or O-benzyl, for example) or an imine 74 (X'=$R^1$) followed by reduction to an amine 75 ($R^{6'}$=H) using a reducing agent such as lithium aluminum hydride or borane, as shown in Scheme 11. Alternatively, the oxime or substituted oxime or imine 74 can be treated with an organometallic reagent such as $R^6 L^1$ or $R^{6'}$MgBr, followed by reductive cleavage of the N—O bond in the cases of oximes or substituted oximes, to provide amines 75 where $R^6$ is one of the $R^6$ substituents. (In the cases of oximes and substituted oximes, the $R^1$ of 75 will be H.) This type of transformation is well known in the literature of organic chemistry. References to some examples are given in R. C. Larock, *Comprehensive Organic Transformations*, VCH, 1989.

Ketones 73 can also be converted to amines by reductive amination, using well-known procedures as discussed previously, to provide amines 76. The same procedure can be used to provide amines 77 useful as intermediates 43, as described in Scheme 6.

Alternatively, ketones 73 can be converted to alcohols 78 by reduction using reagents such as sodium borohydride or lithium aluminum hydride. The alcohols 78 can be converted to the primary amines 76 ($R^1$=H) using several methods, for instance, by conversion of the hydroxyl group to a leaving group such as methanesulfonate, trifluoromethanesulfonate or p-toluenesulfonate; displacement of the leaving group with an appropriate nucleophile such as azide anion; and reduction of the resulting azide to an amine using, for example, a method such as catalytic hydrogenation or reduction with triphenylphosphine followed by hydrolysis of the intermediate iminophosphorane with water. Examples of these transformations can be found in K. Hilpert et al., J. Med. Chem. 1994, 37, 3889; C. Lebarbier et al., Synthesis 1996, 1371; and M. Rubiralta et al., Synth. Commun., 1992, 22, 359. The alcohols 78 can also be converted directly to the corresponding azides with reagents such as hydrazoic acid or diphenylphosphoryl azide in the presence of a dialkyl azodicarboxylate and triphenylphosphine, for example, as described in B. Lal et al., Tetrahedron Lett. 1977, 1977; or J. Hiebl et al., J. Med. Chem. 1991, 34, 1426.

Scheme 11

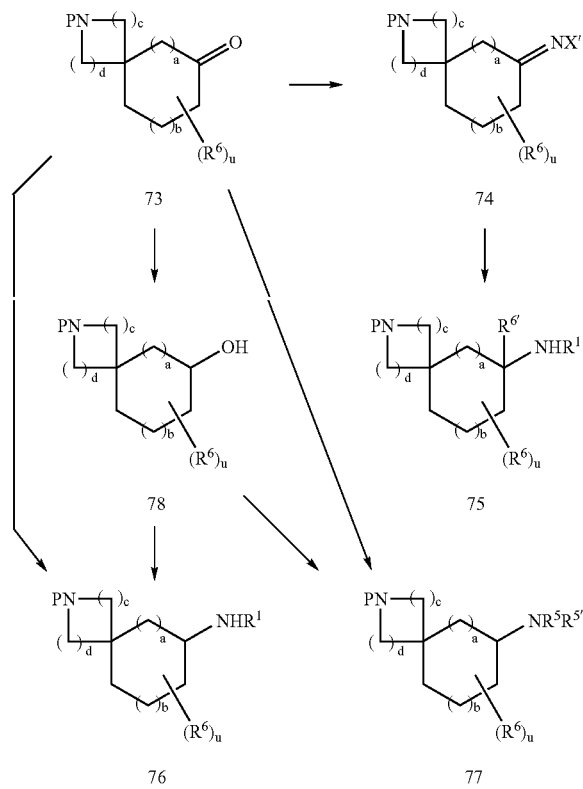

Ketones 73 (equivalent to 46 in Scheme 6) may be prepared using a wide variety of synthetic methods as reported in the literature of organic chemistry. For example, the carboxylic acids 68 (R=OH) show in Scheme 10 may be converted to the corresponding ketones 73 using the oxidative decarboxylation method reported by H. Wasserman and B. H. Lipshutz, Tetrahedron Lett., 1975, 4611. Numerous other methods have been reported for preparation of the bicyclic ring systems corresponding to the ketones 73, with various substitution on the rings and various protecting groups or substitution on the ring nitrogen. In some cases, the reported methods can directly yield the desired ketones 73. In other cases, minor modifications of the reported methods, which will be obvious to one skilled in the art of organic synthesis, can yield the desired ketones 73. In still other cases, simple synthetic transformations of the reported products, obvious to one skilled in the art, can yield the desired ketones 73. For example, in many cases the cyclic amine can be produced as a lactam, in which case reduction of the lactam to the corresponding amine can be achieved using a variety of methods well known to one skilled in the art. Some examples of such methods are listed below. It should be noted that in some cases the ketone of 73 may be replaced by a hydroxyl or amino group, suitably protected if necessary, prior to formation of the spiro ring system as described below.

Ketones 73 (a=0; c=0; d=2) can be prepared by by radical cyclization of a 2-haloacetylamino-1-phenylthiocycloalkene, followed by subsequent synthetic manipulations, as described by H. Ishibashi et al., Tetrahedron 2001, 57, 7629, and H. Ishibashi et al., Tetrahedron Lett. 1998, 39, 75, or by photocyclization of a 2-acylaminocycloalk-2-en-1-one followed by subsequent manipulations, as described by M. Ikeda et al., Chem. Pharm. Bull. 1986, 34, 4997. Ketones 73 (a=0; c=0; d=3 or 4) can be prepared by Dieckmann cyclization of a 2-alkoxycarbonyl-2-(alkoxycarbonylalkyl)-pyrrolidine or piperidine, as reported by P. Duhamel and M. Kotera, J. Org. Chem. 1982, 47, 1688. Ketones 73 (a=0; c=0; d=3) can also be prepared by radical cyclization of a 2-acrylylaminocycloalk-2-en-1-one (A. F. Parsons and D. A. J. Williams, Tetrahedron 1998, 54, 13405) followed by reduction of the resulting lactam; by reduction of a protected 2-nitro-2-alkoxycarbonylethylcyclohexan-1-one with concomitant cyclization, followed by reduction of the resulting lactam and deprotection (M. Sawamura et al., J. Org. Chem. 1996, 61, 9090); or by cyclization of a protected 2-(3-aminopropyl)-1, 2-epoxycyclohexane followed by oxidation of the resulting alcohol (R. A. Fujimoto et al., J. Med. Chem. 1989, 32, 1259).

Ketones 73 (a=0; c=0; d=4) can be prepared by a semipinacol rearrangement of a protected 2-(1-hydroxycycloalkyl)-1,4,5,6-tetrahydropyridine, as reported by M. D. B. Fenster, B. O. Patrick and G. R. Dake (Org. Lett. 2001, 3, 2109); by cyclization of a 1,3-diacetoxy-2-amino-2-alkoxycarbonyl-propylcycloalkane followed by subsequent synthetic manipulations, as described by F. A. Luzzio and R. W. Fitch (J. Org. Chem. 1999, 64, 5484); by cyclization of a 2-amino-2-(3-trialkylsilyl-2-propenyl)cycloalkanone and subsequent reduction, as reported by P. Compain, J. Gore and J.-M. Vatele, Tetrahedron 1996, 52, 6647; by ozonolysis of a protected 4 a-amino-2,3,4,4 a,5,6,7,8-octahydronaphthalene followed by cyclization and reduction of the resulting protected enamine (A. B. Holmes et al., Tetrahedron Lett. 1984, 25, 4163); or by Beckmann rearrangement of the oxime of a protected spirobicyclo[5.4]decan-1,6-dione followed by reduction of the resulting lactam (F. T. Bond, J. E. Stemke and D. W. Powell, Synthetic Commun. 1975, 5, 427).

Ketones 73 (a=0; c=1; d=2 or 3) can be prepared by radical cyclization of an N-(allyl or 4-butenyl)-cycloalkanone-2-carboxamide, or an enamine thereof, followed by reduction of the resulting lactam, as reported by J. Cossy, A. Bouzide and C. LeBlanc (J. Org. Chem. 2000, 65, 7257) and by J. Cossy, A. Bouzide and M. Pfau (J. Org. Chem. 1997, 62, 7106). Ketones 73 (a=0; c=1; d=3) can also be prepared by alkylation of the dianion of an alkyl 2-hydroxycycloalkane-1-carboxylate with a protected 3-bromopropylamine, followed by deprotection, cyclization, reduction of the resulting lactam and oxidation of the alcohol, as reported by M. Keppens and N. De Kimpe (J. Org. Chem. 1995, 60, 3916); by cyclization of an alkyl 2-(3-aminopropyl)-cycloalkanone-2-carboxylate followed by reduction of the resulting lactam (M. Fujii et al., Chem. Lett. 1992, 8, 1493); by Mannich cyclization of a protected 2-(3-aminopropyl)cycloalkanone as reported by W. Carruthers and R. C. Moses (J. Chem. Soc. Chem. Commun. 1987, 509), or by reductive amination of a protected 2-formyl-2-(2-formylethyl)cycloalkanone with a suitable amine.

Ketones 73 (a=1; c=0; d=2, 3, or 4) can be prepared by radical cyclization of a protected 3-(phenylselenylalkyl)amino-cycloalk-2-en-1-one, as described by D. S. Middleton, N. S. Simpkins and N. K. Terrett, Tetrahedron Lett. 1989, 30, 3865. Ketones 73 (a=1; c=0; d=3) can also be prepared by treatment of a 3-(2-alkoxycarbonylethyl)cycloalk-2-en-1-one with a primary amine, followed by reduction of the resulting lactam (L. F. Tietze and P. L. Steck, Eur. J. Org. Chem. 2001, 22, 4353); by photoinduced cyclization of a protected 3-(3,4-pentadienyl)aminocycloalk-2-en-1-one followed by ozonolysis and reduction (M. S. Shephard and E. M. Carreira, Tetrahedron 1997, 53, 16253); or by cyclization of a 3-allylaminocycloalk-2-en-1-one or derivative thereof followed by subsequent synthetic manipulations (T. Tiner-Harding et al., J. Org. Chem. 1982, 47, 3360).

Ketones 73 (a=1; c=0; d=4) can also be prepared by dissolving metal reduction of a 3-(4-aminobutyl)-1-anisole, followed by acidic hydrolysis (J. J. Venit, M. DiPierro and P. Magnus, J. Org. Chem. 1989, 54, 4298), or by cyclization of a 3-(4-aminobutyl)cycloalk-2-en-1-one, as reported by S. A. Godleski and D. J. Heacock, J. Org. Chem. 1982, 47, 4820). Ketones 73 (a=1; c=1; d=1) can be prepared by photoinduced cyclization of a 3-(N-alkylaminocarbonyl)-cycloalk-2-en-1-one, followed by reduction of the resulting lactam, as reported by F. Toda et al., J. Org. Chem. 1993, 58, 6208. Ketones 73 (a=1; c=1; d=2) can be prepared by photoinduced cyclization of a 3-(2-(N-trialkylsilylmethylamino)ethyl)-cycloalk-2-en-1-one (W. Xu et al., J. Amer. Chem. Soc. 1989, 111, 406). Ketones 73 (a=1; c=1; d=3) can be prepared by photoinduced (2+2)cycloaddition of a 3-(5-trialkylsilylpent-3-enylaminocarbonyl)-cycloalk-2-en-1-one, followed by cyclobutane ring cleavage and subsequent synthetic transformations, as described by S. Faure, S. Piva-LeBlanc and O. Piva, Tetrahedron Lett. 1999, 40, 6001.

Ketones 73 (a=0) can also be prepared as shown in Scheme 12. In Scheme 12, b=2, although the same synthetic route can be used to prepare ketones 73 with b=1 or b=3. An ester 79 (R'=alkyl) can be treated with a strong base, and the resulting anion can be alkylated with, for example, an optionally substituted allyl bromide, to provide 80. The ester can then be converted to an aldehyde 81 using methods known to one skilled in the art of organic synthesis. Reaction of 81 with an alkenyl organometallic reagent such as, for example, an optionally substituted allyl magnesium halide, can provide an alcohol 82. This diolefin can be cyclyzed using ring-closing metathesis, a reaction well known in the literature of organic synthesis, to provide the spirocyclic alkene 83. Reduction of the double bond and oxidation of the alcohol can provide the ketone 84, which is equivalent to the ketone 73 with a=0 and b=2.

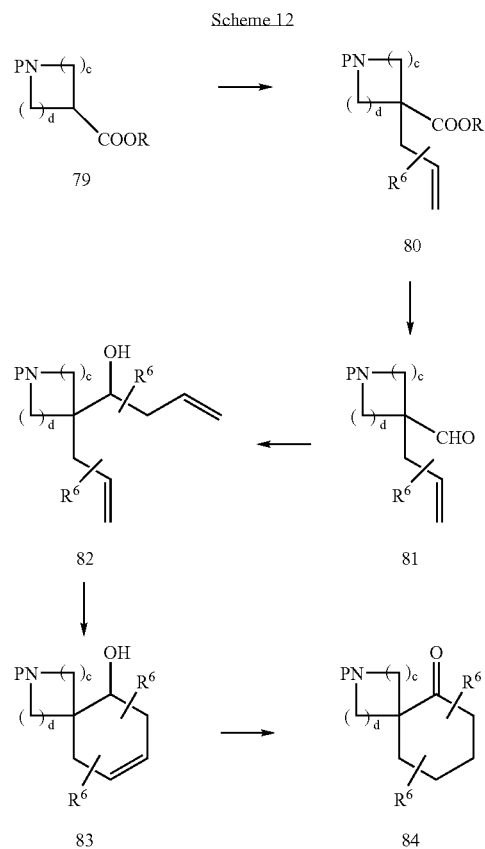

Scheme 12

Many of the alkylating agents $R^5$—X (2), aldehydes and ketones RC(=O)R' (9) and acylating agents RC(=O)X (21) used to install the $R^5$ substituent into the compounds of Formula (Ia) and Formula (Ib), for example as shown in Schemes 1 and 2 are commercially available or are well known in the art of organic chemistry, and methods for their preparation are well known and well exemplified. Such alkylating agents, aldehydes and ketones, acylating agents, and amines which have not been previously reported can be prepared using methods reported for the preparation of closely analogous compounds, and many other methods well known in the art. Such methods are reviewed in many well-known reference works, for example R. C. Larock, *Comprehensive Organic Transformations*, VCH, 1989; A. Katritzky et al. (series editors), *Comprehensive Organic Functional Group Transformations*, Pergamon, 1995; and B. Trost and I. Fleming (series editors), *Comprehensive Organic Synthesis*, Pergamon, 1991. Methods for producing these compounds using such known methods will be obvious to one skilled in the art.

EXAMPLES

Example 1

Part A: Preparation of 2-(S-1-phenylethylamino)-cyclohex-1-enecarboxylic acid ethyl ester A solution of 2-oxocyclohexanecarboxylic acid ethyl ester in benzene (200 mL) was treated with (S)-1-phenyl-ethylamine (61.8 g, 0.51 mol) and ytterbium (III) triflate (0.6 g) and heated to reflux for 2-3 hours with the removal of water with a Dean-Stark trap. The resulting solution was concentrated to give 27.5 g of an oil. $^1$H NMR (300 MHz, CDCl$_3$) δ9.41 (d, J=7 Hz, 1H), 7.35-7.19 (m, 5H), 4.67-4.58 (m, 1H), 4.16 (q, J=7 Hz, 2H), 2.38-2.21 (m, 3H), 1.96-1.88 (m, 1H), 1.60-1.40 (m, 4H), 1.47 (d, J=7 Hz, 3H), 1.29 (t, J=7 Hz, 3H).

Part B: Preparation of (1S)-1-(2-ethoxycarbonyl-ethyl)-2-oxocyclohexanecarboxylic acid ethyl ester To a suspension of magnesium bromide diethyl etherate (5.16 g, 20 mmol) in ether (20 mL) was added dropwise a solution of 2-(S-1-phenylethylamino)-cyclohex-1-enecarboxylic acid ethyl ester (5.46 g, 20 mmol) and ethyl acrylate (3.0 g, 30 mmol) in ether (20 mL). The resulting suspension was stirred at room temperature for 2 hours and then treated with 50 mL of 10% aqueous acetic acid. The acid mixture was stirred at room temperature for 48 hours.

The mixture was made basic with 1.0 N aqueous sodium hydroxide and the aqueous phase was extracted with ether. The combined ether extracts were washed with saturated aqueous sodium chloride, dried over sodium sulfate, and concentrated to give a residue. The residue was chromatographed on silica gel, eluting with 15% ethyl acetate/hexane, to give 4.2 g of an oil. $^1$H NMR (300 MHz, CDCl$_3$) δ4.25-4.16 (m, 2H), 4.12 (q, J=7 Hz, 2H), 2.58-2.36 (m, 4H), 2.34-2.16 (m, 2H), 2.08-1.83 (m, 2H), 1.80-1.60 (m, 3H), 1.55-1.38 (m, 1H), 1.30-1.22 (m, 6H).

Part C: Preparation of (1S,2R)-1-(2-ethoxycarbonyl-ethyl)-2-(1R-phenylethylamino)-cyclohexanecarboxylic acid isopropyl ester A mixture of (1S)-1-(2-ethoxycarbonylethyl)-2-oxocyclohexanecarboxylic acid ethyl ester (4.2 g, 16 mmol), 1-(R)-phenylethylamine (1.9 g, 16 mmol) and titanium (IV) isopropoxide (8.8 g, 0.031 mmol) was stirred at room temperature for 1.5 hours. The solution was quenched with 0.1 N aqueous sodium hydroxide (25 ml) and stirred for 30 minutes. The resulting suspension was filtered through Celite and the filter cake was washed several times with dichloromethane. The combined organic filtrates were washed with saturated aqueous sodium chloride, dried, and concentrated to give 2.2 grams of crude product. The crude product was purified by chromatography on silica gel, eluting with 35% ethyl acetate/hexane, to give 1.0 g of a colorless oil. $^1$H NMR (300 MHz, CDCl$_3$) δ7.32-7.19 (m, 5H), 5.02 (heptet, J=6.2 Hz, 1H), 4.16 (q, J=7 Hz, 2H), 3.75 (q, J=7 Hz, 1H), 3.06 (m, 1H), 2.40 (m, 1H), 2.16 (m, 2H), 1.84 (m, 2H), 1.49-1.18 (m, 16H). Mass spec (ES+) m/z 390.3 (M+H$^+$, 100%).

Part D: Preparation of 3-[(1S,2R)-1-hydroxymethyl-2-(1R-phenylethylamino)-cyclohexyl]-propan-1-ol A solution of (1S,2R)-1-(2-ethoxycarbonylethyl)-2-(1R-phenylethylamino)-cyclohexanecarboxylic acid isopropyl ester (1.1 g, 2.8 mmol) in ether (50 mL) was cooled to 0° C. in an ice bath and treated slowly with lithium aluminum hydride (0.46 g, 12 mmol). After the addition was complete, the mixture was stirred for an additional 45 minutes and then quenched by dropwise addition of water (0.5 mL) followed by slow, careful addition of 1.0 N aqueous sodium hydroxide (2 mL). The resulting suspension was stirred in the ice bath for 1-2 hours to give a granular white suspension, which was removed by filtration and washed with ether. The combine ether filtrates were concentrated to give 0.82 g of a colorless syrup. $^1$H NMR (300 MHz, CDCl) δ7.35-7.24 (m, 5H), 3.85 (q, J=7 Hz, 1H), 3.65 (t, J=6 Hz, 2H), 3.50 (dd, J=9, 16 Hz, 2H), 2.61 (m, 1H), 1.83 (m, 1H), 1.72 (m, 1H), 1.63-1.09 (m, 9H), 1.39 (d, J=7 Hz, 3H), 0.76 (m, 1H).

Part E: Preparation of [(1R, 2S)-2-hydroxymethyl-2-(3-hydroxypropyl)-cyclohexyl]-carbamic acid benzyl ester A solution of 3-[(1S,2R)-1-hydroxymethyl-2-(1R-phenylethylamino)-cyclohexyl]-propan-1-ol (0.82 g, 2.8 mmol) in methanol (50 mL) was treated with 20% palladium hydroxide on carbon (0.5 g) and hydrogenated overnight at 55 psi. The mixture was filtered through Celite and concentrated to give 0.55 g of a thick syrup. A solution of the thick syrup (0.53 g, 2.8 mmol) in dichloromethane (50 mL) was treated with an aqueous solution of potassium carbonate (1.0 g, 8 mmol) and cooled in an ice bath. The mixture was stirred vigorously while benzyl chloroformate (0.75 g, 4.4 mmol) was added dropwise. After the addition was complete, the mixture was stirred for an additional 30 min. The organic phase was separated and washed with water and saturated aqueous sodium chloride, and concentrated to give a solid. The solid was purified by chromatography on silica gel, eluting with 75% ethyl acetate/hexane, to give 0.65 g of a white solid. $^1$H NMR (300 MHz, CDCl) δ7.38-7.32 (s, 5H), 5.08 (d, J=2 Hz, 2H), 4.80 (d, J=9 Hz, 1H), 3.99-3.95 (m, 1H), 3.74 (m, 1H), 3.61 (m, 2H), 3.40-3.36 (m, 1H), 3.26-3.19 (m, 1H), 1.78-0.96 (m, 13H). Mass spec (ES+) m/z 322.2 (M+H$^+$, 100%).

Part F: Preparation of [(1R,2S)-2-formyl-2-(3-oxo-propyl)-cyclohexyl]-carbamic acid benzyl ester A solution of dimethyl sulfoxide (1.6 g, 19 mmol) in dichloromethane (50 mL) was cooled to −78° C. and treated dropwise with oxalyl chloride (1.42 g, 11.2 mmol). After the addition was complete, the solution was stirred for 30 minutes and was then treated dropwise with a solution of [(1R,2S)-2-hydroxymethyl-2-(3-hydroxypropyl)-cyclohexyl]-carbamic acid benzyl ester (0.65 g, 1.9 mmol) in dichloromethane (10 mL). After the addition was complete, the solution was stirred for 40 minutes and then treated with triethylamine (1.8 g, 18 mmol). The mixture was stirred for 30 minutes before removing the cooling bath and stirring at room temperature for 1 hour. The mixture was quenched with saturated aqueous sodium bicarbonate (100 mL) and the organic phase was separated and washed successively with water and saturated aqueous sodium chloride, and then dried over sodium sulfate. The solvent was removed under vacuum to give an oil (0.6 g). $^1$H NMR (300 MHz, CDCl$_3$) δ9.74 (bs, 1H), 9.43 (bs, 1H), 7.39-7.27 (m, 5H), 5.06 (m, 2H), 4.91 (bd, J=9 Hz, 1H), 4.14 (bm, 1H), 2.60-1.30 (m, 12H). Mass spec (ES+) m/z 318.2 (M+H$^+$, 100%).

Part G: Preparation of {2-[2-(4-Fluoro-phenyl)-ethyl]-2-aza-spirof[5.5]undec-7-yl}-carbamic acid benzyl ester A solution of [(1R,2S)-2-formyl-2-(3-oxo-propyl)-cyclohexyl]-carbamic acid benzyl ester (0.6 g, 1.9 mmol) and 2-(4-fluorophenyl)-ethylamine (0.3 g, 2.1 mmol) in dichloromethane (50 mL) was cooled in an ice bath and treated with sodium triacetoxyborohydride (0.6 g, 2.8 mmol). The mixture was stirred at room temperature for 2 hours. After this time, 1.0 N aqueous sodium hydroxide (25 mL) was added, and the mixture was stirred at room temperature for 1 hour. The organic phase was separated and washed with water and saturated aqueous sodium chloride. The solvent was removed under vacuum to give a residue. The residue was purified by chromatography on silica gel, eluting with 80% ethyl acetate/hexane, to give the desired product (0.60 g). $^1$H NMR (300 MHz, CDCl$_3$) δ(TMS): 7.39-7.26 (m, 5H), 7.16-7.05 (m, 2H), 7.00-6.91 (m, 2H), 5.10 (m, 3H), 3.63 (bm, 1H), 2.80-2.00 (m, 8H), 1.85-1.05 (m, 12H). Mass spec (ES+) m/z 425.3 (M+H+, 100%).

Part H: Preparation of 2-[2-(4-fluorophenyl)-ethyl]-2-aza-spiro[5.5]undec-7-ylamine A solution of {2-[2-(4-fluoro-phenyl)-ethyl]-2-aza-spiro[5.5]undec-7-yl}-carbamic acid benzyl ester (0.60 g, 1.4 mmol) in methanol (30 mL) was treated with 10% palladium on carbon (1.0 g) and shaken under a hydrogen atmosphere (60 psig) for 20 hours at room temperature. The catalyst was removed by filtration and the solvent was removed under vacuum to give a white foam (0.35 g).

Part I: Preparation of N-methyl-3-nitrobenzamide

3-Nitrobenzoyl chloride (7.00 g, 37.7 mmol) was dissolved in tetrahydrofuran (300 mL) and a 2.0 M solution of methylamine in tetrahydrofuran (41.5 mL, 82.9 mmol) was added. The reaction mixture was stirred for 2 hours. The reaction mixture was diluted with ethyl acetate and washed three times with water. The organic layer was dried over sodium sulfate and concentrated to provide a solid (6.38 g, 94%). $^1$H NMR (300 MHz, CDCl$_3$), δ8.84 (bs, 1H), 8.67 (m, 1H), 8.37 (dd, J=8, 2 Hz, 1H), 8.28 (d, J=7 Hz, 1H), 7.78 (dd, J=8, 7 Hz, 1H), 2.83 (m, 3H). Mass spec (ES+) m$^+$/z 181 (M+H$^+$).

Part J: Preparation of 1-methyl-5-(3-nitrophenyl)-tetrazole

N-Methyl-3-nitro-benzamide (30.0 g, 167 mmol) was dissolved in acetonitrile (835 mL). Upon dissolution, sodium azide (10.9 g, 167 mmol) was added. The mixture was cooled in an ice bath, and trifluoromethanesulfonic anhydride (29 mL, 172 mmol) was added dropwise at a rate to maintain the reaction temperature below 3° C. The reaction mixture was stirred for 3.5 hours at 0° C. and then poured into 1N aqueous sodium hydroxide (100 mL). The organic layer was separated, dried over sodium sulfate and concentrated under vacuum to 50 mL. The solution was diluted with dichloromethane and water was added. The resuling precipitate was isolated by filtration to give a yellow solid (18.46 g, 54%). The filtrate was concentrated in vacuo and added to boiling ethyl acetate to give a second crop of crystals. Upon cooling to 0° C., additional material (6.07 g, 18%) was isolated by filtration. $^1$H NMR (300 MHz, CDCl$_3$), δ8.67 (m, 1H), 8.49 (dd, J=8, 2 Hz, 1H), 8.31 (d, J=8 Hz, 1H), 7.94 (dd, J=8, 8 Hz, 1H), 4.22 (s, 3H).

Part K: Preparation of 1-methyl-5-(3-aminophenyl)-tetrazole

1-Methyl-5-(3-nitrophenyl)-tetrazole (28.8 g, 140 mmol) was dissolved in ethyl acetate (430 mL) and methanol (1270 mL). Palladium on carbon (2.7 g, 10 wt %) was added and the mixture was shaken under a hydrogen atmosphere (60 psig) for 1.5 hours. The mixture was filtered, and the filtrate was concentrated under vacuum to give a white solid (24.0 g, 98%). $^1$H NMR (300 MHz, CDCl$_3$), δ7.21 (dd, J=8, 7 Hz, 1H) 6.99 (s, 1H), 6.90 (d, J=7 Hz, 1H), 6.76 (d, J=8 Hz, 1H), 5.44 (bs, 2H), 4.10 (s, 3H).

Part L: Preparation of [3-(1-methyl-1H-tetrazol-5-yl)-phenyl]-carbamic acid phenyl ester 1-Methyl-5-(3-aminophenyl)-tetrazole (24.0 g, 137 mmol) was dissolved in dichloromethane (1.4 L) and 2,6-lutidine (44.1 g, 411 mmol) was added. Phenyl chloroformate (21.2 g, 136 mmol) was added in 4 portions over 15 minutes, and the mixture was stirred for 1.5 hours. The mixture was poured into 1N aqueous hydrochloric acid (200 mL) and the mixture was extracted three times with dichloromethane (200 mL). The combined organic layers were washed with saturated aqueous sodium chloride, dried over sodium sulfate, and concentrated under vacuum to give a crude brown material. The crude brown material was dissolved in hot toluene, filtered, and allowed to precipitate at 0° C. to give a white solid (34.1 g). The filtrate was concentrated and recrystallized again from toluene to give an additional crop of off-white crystals (3.44 g, 93% total). $^1$H NMR (300 MHz, CDCl$_3$), δ10.51 (bs, 1H), 8.01 (s, 1H), 7.71 (dt, J=7, 2 Hz, 1H), 7.55 (m, 2H), 7.41 (m, 2H), 7.24 (m, 2H), 4.14 (s, 3H).

Part M: Preparation of 1-{(7R,6S)-2-[2-(4-fluorophenyl)-ethyl]-2-azaspiro[5,5]undec-7-yl}-3-[3-(1-methyl-1H-tetrazol-5-yl)-phenyl]-urea A solution of 2-[2-(4-fluoro-phenyl)-ethyl]-2-aza-spiro[5.5]undec-7-ylamine (50 mg, 0.172 mmol) in tetrahydrofuran (2 mL) was treated with [3-(1-methyl-1H-tetrazol-5-yl)-phenyl]carbamic acid phenyl ester (64 mg, 0.22 mmol), and the mixture was stirred at room temperature overnight. The solvent was removed under vacuum and the resulting solid was purified by chromatography on silica gel, eluting first with 0.2:1.8:98 ammonium hydroxide/methanol/dichloromethane, then with 0.8:7.2:92 ammonium hydroxide/methanol/dichloromethane, to provide the desired product (40 mg). $[\alpha]_D^{25}=-64.3°$ (c=0.310, chloroform). $^1$H NMR (300 MHz, CDCl$_3$) δ8.34 (bs, 1H), 7.90 (d, J=9 Hz, 1H), 7.82 (bs, 1H), 7.37 (t, J=8 Hz, 1H), 7.20 (d, J=7 Hz, 1H), 7.15-7.09 (m, 2H), 6.96-6.89 (m, 2H), 6.25 (bs, 1H), 4.16 (s, 3H), 3.92 (bs, 1H), 2.71 (m, 2H), 2.60 (m, 1H), 2.45 (m, 2H), 2.31 (m, 1H), 2.12 (m, 1H), 1.95-1.10 (m, 13H). Mass spec (ES+) m$^+$/z 492.4 (M+H$^+$).

Example 2

Part A: Preparation of [(1R, 2S)-2-hydroxymethyl-2-(3-hydroxypropyl)-cyclohexyl]-carbamic acid tert-butyl ester A solution of 3-((1S,2R')-2-amino-1-hydroxymethylcyclohexyl)-propan-1-ol (prepared as described in Example 1, Part E, 3.7 g, 20 mmol) in dichloromethane (50 mL) was treated with triethylamine (3.0 g, 30 mmol) and di-tert-butyl dicarbonate (4.7 g, 23 mmol). The solution was stirred at room temperature for 1 hour and concentrated on a rotary evaporator to give a residue. The residue was purified by chromatography on silica gel, eluting with ethyl acetate, to give a white solid (4.8 g). $^1$H NMR (300 MHz, CDCl$_3$) δ4.45 (m, 1H), 4.20 (m, 1H), 3.63 (m, 3H), 3.37 (m, 1H), 3.22 (m, 1H), 1.80-0.98 (m, 13H), 1.44 (s, 9H).

Part B: Preparation of [(1R,2S)-2-formyl-2-(3-oxo-propyl)-cyclohexyl]-carbamic acid tert-butyl ester A solution of dimethyl sulfoxide (16 g, 180 mmol) in dichloromethane (60 mL) was cooled to −78° C. in a cooling bath and treated dropwise with oxalyl chloride (14.2 g, 112 mmol). After the addition was complete, the solution was stirred for 30 minutes and then treated dropwise with a solution of [(1R,2S)-2-hydroxymethyl-2-(3-hydroxypropyl)-cyclohexyl]-carbamic acid tert-butyl ester (4.8 g, 16.7 mol) in dichloromethane (100 mL). After the addition was complete, the solution was stirred for 40 minutes and then treated with triethylamine (19 g, 190 mmol). The mixture was stirred for 30 minutes. The cooling bath was removed and the mixture was allowed to warm to room temperature where it stirred for 1 hour. The mixture was quenched with saturated aqueous sodium bicarbonate (100 mL). The organic phase was removed, washed successively with water and saturated aqueous sodium chloride, and then dried over sodium sulfate. The solvent was removed under vacuum to give an oil (4.75 g). $^1$H NMR (300 MHz, CDCl$_3$) δ9.78 (s, 1H), 9.41 (s, 1H), 4.56 (bd, J=9 Hz, 1H), 4.05 (m, 1H), 2.60-1.30 (m, 21H).

Part C: Preparation of [(6S,7R)-2-(4-fluorobenzyl)-2-aza-spiro[5,5]undec-7-yl]-carbamic acid tert-butyl ester A solution of [(1R,2S)-2-formyl-2-(3-oxo-propyl)-cyclohexyl]-carbamic acid tert-butyl ester (4.73 g, 16.7 mmol) and 4-fluorobenzylamine (2.3 g, 18 mmol) in dichloromethane (50 mL) was cooled in an ice bath and treated with sodium triacetoxyborohydride (10.1 g, 48 mmol). The resulting mixture was then stirred at room temperature overnight. The mixture was treated with 1.0 N aqueous sodium hydroxide (25 mL) and stirred at room temperature for 1 hour. The organic phase was removed and washed with water and saturated aqueous sodium chloride. The solvent was removed under vacuum to give a residue. The residue was purified by chromatography on silica gel, eluting with 60% ethyl acetate/hexane, to give an oil (6.3 g). $^1$H NMR (300 MHz, CDCl$_3$) δ7.31-7.24 (m, 2H), 6.97-6.94 (m, 2H), 4.82 (bm, 1H), 3.62 (m, 1H), 3.37 (bs, 2H), 2.42 (m, 1H), 2.20 (m, 3H), 1.69-1.21 (m, 12H), 1.45 (s, 9H). Mass spec (ES+) m$^+$/z 377.2 (M+H$^+$).

Part D: Preparation of (6S,7R)-2-(4-fluorobenzyl)-2-aza-spiro[5,5]undec-7-ylamine A solution of [(6S,7R)-2-(4-fluorobenzyl)-2-aza-spiro[5.5]undec-7-yl]-carbamic acid tert-butyl ester (6.3 g, 1.4 mmol) in dichloromethane (30 mL) was treated with trifluoroacetic acid (30 mL) and stirred at room temperature for 1 hour. The solvent was removed under vacuum to give a residue. The residue was treated with 1.0 N aqueous sodium hydroxide. The mixture was extracted with dichloromethane and the organic phase was washed with water and saturated aqueous sodium chloride. The solvent was removed under vacuum to give an oil (4.2 g). $^1$H NMR (300 MHz, CDCl$_3$) δ7.30-7.24 (m, 2H), 7.01-6.94 (m, 2H), 3.37 (m, 2H), 2.62 (m, 1H), 2.44 (m, 1H), 2.24 (m, 2H), 2.09 (m, 1H), 1.81 (m, 1H), 1.65-1.24 (m, 13H). Mass spec (ES+) m$^+$/z 277.2 (M+H$^+$).

Part E: Preparation of 1-{(7R,6S)-2-(4-fluorobenzyl)-2-aza-spiro[5.5]undec-7-yl}-3-[3-(1-methyl-1H-tetrazol-5-yl)-phenyl]-urea A solution of (6S,7R)-2-(4-fluorobenzyl)-2-aza-spiro[5.5]undec-7-ylamine (90 mg, 0.32 mmol) in tetrahydrofuran (2 mL) was treated with [3-(1-methyl-1H-tetrazol-5-yl)-phenyl]-carbamic acid phenyl ester (123 mg, 0.42 mmol), and the mixture was stirred at room temperature overnight. The solvent was removed under vacuum and the resulting solid was purified by chromatography on silica gel, eluting with 0.2:1.8:98 ammonium hydroxide/methanol/dichloromethane, to give the desired product (80 mg). $^1$H NMR (300 MHz, CDCl$_3$) δ8.27 (bs, 1H), 7.94 (d, J=9 Hz, 1H), 7.82 (bs, 1H), 7.39 (t, J=8 Hz, 1H), 7.26-7.19 (m, 3H), 6.98-6.91 (m, 2H), 6.21 (bs, 1H), 4.17 (s, 3H), 3.98 (bs, 1H), 3.35 (m, 2H), 2.50-2.15 (m, 3H), 1.85 (m, 2H), 1.65-1.20 (m, 11H). Mass spec (ES+) m$^+$/z 478.4 (M+H$^+$).

Representative compounds prepared by the methods disclosed above are listed in Tables 1 and 2.

TABLE 1

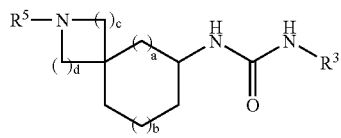

where a is 0 and b is 2;

| Example | c | d | R$^3$ | R$^5$ | Mass spec, (M + H)$^+$ |
|---|---|---|---|---|---|
| 1 | 1 | 3 | 3-(1-methyl-tetrazol-5-yl)-C$_6$H$_4$ | 4-F—C$_6$H$_4$—(CH$_2$)$_2$— | 492 |
| 2 | 1 | 3 | 3-(1-methyl-tetrazol-5-yl)-C$_6$H$_4$ | 4-F—C$_6$H$_4$—CH$_2$— | 478 |
| 3 | 2 | 2 | 3-(1-methyl-tetrazol-5-yl)-C$_6$H$_4$ | 4-F—C$_6$H$_4$—(CH$_2$)$_3$— | 506 |
| 4 | 2 | 2 | 3-(1-methyl-tetrazol-5-yl)-C$_6$H$_4$ | 4-F—C$_6$H$_4$—(CH$_2$)$_2$— | 492 |
| 5 | 2 | 2 | 3-(1-methyl-tetrazol-5-yl)-C$_6$H$_4$ | 4-Cl—C$_6$H$_4$—(CH$_2$)$_2$— | 508 |
| 6 | 2 | 2 | 3-(1-methyl-tetrazol-5-yl)-C$_6$H$_4$ | C$_6$H$_4$—(CH$_2$)$_3$— | 488 |
| 7 | 2 | 2 | 3-(1-methyl-tetrazol-5-yl)-C$_6$H$_4$ | 2,4-Cl$_2$—C$_6$H$_4$—(CH$_2$)$_2$— | 542 |

TABLE 1-continued where a is 0 and b is 2;

| Example | c | d | R³ | R⁵ | Mass spec, (M + H)⁺ |
|---|---|---|---|---|---|
| 8 | 2 | 2 | 3-(1-methyl-tetrazol-5-yl)-C₆H₄ | C₆H₄—CH=CHCH₂— | 486 |
| 9 | 2 | 2 | 3-(1-methyl-tetrazol-5-yl)-C₆H₄ | 4-Cl—C₆H₄—(CH₂)₃— | 522 |
| 10 | 1 | 3 | 4-methyl-5-acetylthiazol-2-yl | 4-F—C₆H₄—(CH₂)₂— | 473 |
| 11 | 1 | 3 | 3-ethyl-5-(1-methyl-tetrazol-5-yl)-C₆H₄ | 4-F—C₆H₄—(CH₂)₂— | 520 |
| 12 | 1 | 3 | 3-ethyl-5-(1-methyl-tetrazol-5-yl)-C₆H₄ | 4-F—C₆H₄—CH₂— | 506 |
| 13 | 1 | 3 | 4-methyl-5-acetylthiazol-2-yl | 4-F—C₆H₄—CH₂— | 459 |

TABLE 2 wherein a is 0; b, c and d are 1;

| Example | R³ | R⁵ | R⁵ᵃ |
|---|---|---|---|
| 14 | 3-ethyl-5-(1-methyl-tetrazol-5-yl)-C₆H₄ | (branched alkyl)-C₆H₄-4F | |
| 15 | 3-acetyl-C₆H₄ | (branched alkyl)-C₆H₄-4F | |
| 16 | 3-acetyl-5-(1-methyl-tetrazol-5-yl)-C₆H₄ | (branched alkyl)-C₆H₄-4F | |
| 17 | 3-ethyl-5-(1-methyl-tetrazol-5-yl)-C₆H₄ | (CH₂)₃—C₆H₄-4F | CH₃ |

Utility

The utility of the compounds in accordance with the present invention as modulators of chemokine receptor activity may be demonstrated by methodology known in the art, such as the assays for CCR-2 and CCR-3 ligand binding, as disclosed by Ponath et al., J. Exp. Med., 183, 2437-2448 (1996) and Uguccioni et al., J. Clin. Invest., 100, 1137-1143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as CHO or HEK-293. Finally, blood or tissue cells, for example human peripheral blood eosinophils, isolated using methods as described by Hansel et al., J. Immunol. Methods, 145, 105-110 (1991), can be utilized in such assays.

The utility of the compounds in accordance with the present invention as inhibitors of the migration of eosinophils or cell lines expressing the chemokine receptors may be demonstrated by methodology known in the art, such as the intracellular calcium measurement (disclosed by Bacon et al., Brit. J. Pharmacol., 95, 966-974 (1988)). In particular, the compounds of the present invention have activity in inhibition of the migration of eosinophils in the aforementioned assays. As used herein, "activity" is intended to mean a compound demonstrating an $IC_{50}$ of 10 µM or lower in concentration when measured in the aforementioned assays. Such a result is indicative of the intrinsic activity of the compounds as modulators of chemokine receptor activity. An intracellular calcium measurement protocol is described below.

Intracellular $Ca^{2+}$ Measurement

Cells ($8 \times 10^5$/mL) were loaded with 4 µM Fluo-3 aM (Molecular Probes, Eugene. Oreg.) in calcium-free PBS containing 0.1% BSA, 1% FBS, 20 mM HEPES, 5 mM glucose and 2.5 mM probenecid) for 60 minutes at 37° C. in the dark. After two washes in buffer (PBS with 0.1% BSA, 20 mM HEPES, 5 mM glucose and 2.5 mM probenecid), cells ($2 \times 10^6$/mL) were resuspended in RPMI containing 0.1% BSA, 20 mM HEPES and 2.5 mM probenecid and plated in 96-well black, clear-bottomed plates (# 3603, Corning, Acton, Mass.), previously coated with poly-D-lysine, at $2 \times 10^5$/well. Individual plates were inserted in a FLIPR (Molecular Devices, Sunnyvale, Calif.). Compound or vehicle (50 µL) was added robotically and incubated for 5 minutes at room temperature, then eotaxin (50 µL) was added for a final concentration of 10 nM. The eotaxin-dependent increase in fluorescence over baseline was recorded in duplicate wells.

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966-974 (1988). In particular, the compounds of the present invention have activity in inhibition of the migration of eosinophils in the aforementioned assays. As used herein, "activity" is intended to mean a compound demonstrating an $IC_{50}$ of 10 µM or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA96 96-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at $1\times10^6$ cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 µl volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30-45 seconds. The filter is rinsed with distilled water for 7 minutes, rinsed once with water briefly, and allowed to dry. Migrated cells are enumerated by microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an $IC_{50}$ of 10 µM or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., Anisaki sp., Phocanema sp.), cutaneous larva migraines (Ancylostona braziliense, Ancylostoma caninum). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selecting, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (1) preparations of interferons (interferon alpha-2 a, interferon-2B, interferon alpha-N3, interferon beta-1 a, interferon beta-lb, interferon gamma-1b); (m) antiviral compounds such as efavirenz, nevirapine, indinavir, ganciclovir, lamivudine, famciclovir, and zalcitabine; (O) other compounds such as 5-aminosalicylic acid and prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula Ia and/or Formula Ib that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice. The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula Ia and/or Formula Ib and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula Ia and/or Formula Ib, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula Ia and/or Formula Ib and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

What is claimed:

1. A compound of formula (Ia):

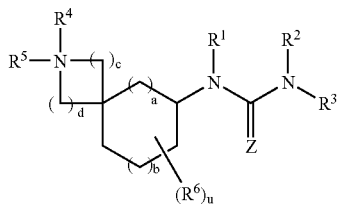

or stereoisomers or pharmaceutically acceptable salts thereof, wherein:

Z is selected from O and S;

$R^1$ and $R^2$ are independently selected from H, $C_{1-8}$ alkyl, $C_{2-8}$ alkenyl, and $C_{2-8}$ alkynyl;

$R^3$ is selected from a $(CR^{3'}R^{3'})_r$—$C_{3-10}$ carbocycle substituted with 0-5 $R^{15}$ and a $(CR^{3'}R^{3'})_r$-5-10 membered heterocyclic system with 1-4 heteroatoms selected from N, O, and S, substituted with 0-3 $R^{15}$;

$R^{3'}$, at each occurrence, is independently selected from H, $C_{1-6}$ alkyl, $(CH_2)_rC_{3-6}$ cycloalkyl, and phenyl;

$R^4$ is absent, taken with the nitrogen to which it is attached to form an N-oxide, or selected from $C_{1-8}$ alkyl, $C_{2-8}$ alkenyl, $C_{2-8}$ alkynyl, $(CH_2)_rC_{3-6}$ cycloalkyl, $(CH_2)_qC(O)R^{4b}$, $(CH_2)_qC(O)NR^{4a}R^{4a}$, $(CH_2)_qC(O)OR^{4b}$, and a $(CH_2)_r$—$C_{3-10}$ carbocycle substituted with 0-3 $R^{4c}$;

$R^{4a}$, at each occurrence, is independently selected from H, $C_{1-6}$ alkyl, $(CH_2)_rC_{3-6}$ cycloalkyl, and phenyl;

$R^{4b}$, at each occurrence, is independently selected from $C_{1-6}$ alkyl, $C_{2-8}$ alkenyl, $(CH_2)_rC_{3-6}$ cycloalkyl, $C_{2-8}$ alkynyl, and phenyl;

$R^{4c}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a}$, and $(CH_2)_r$phenyl;

$R^5$ is selected from

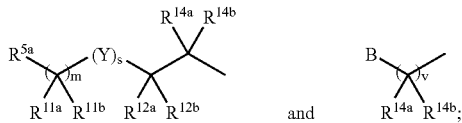

Y is selected from O, $N(R^{25})$, S, S(O), and $S(O)_2$;

ring B is a 5-7 membered cycloalkyl ring with containing a C=O, and being substituted with 0-2 $R^{11a}$, wherein the cycloalkyl ring is fused with a benzo group substituted with 0-3 $R^{16}$ or is fused with a 5-6 membered aromatic heterocyclic ring with 0-3 N, 0-1 O, or 0-1 S, the heterocyclic ring being substituted with 0-3 $R^{16}$;

alternatively, ring B is a 5-7 membered saturated heterocyclic ring with 0-1 O, $N(R^{25})$, S, S(O), and $S(O)_2$, substituted with 0-2 $R^{11a}$, wherein the heterocyclic ring is fused with a benzo group substituted with 0-3 $R^{16}$ or is fused with a 5-6 membered aromatic heterocyclic ring with 0-3 N, 0-1 O, or 0-1 S, the heterocyclic ring being substituted with 0-3 $R^{16}$;

provided that if ring B is a heterocyclic ring, then the number of carbon atoms separating the heteroatom of ring B and the nitrogen atom of formula (Ia) bonded to $R^5$ is at least 2;

$R^{5a}$ is selected from a $C_{3-10}$ carbocycle substituted with 0-5 $R^{16}$, and a 5-10 membered heterocyclic system with 1-4 heteroatoms selected from N, O, and S, substituted with 0-3 $R^{16}$;

$R^6$, at each occurrence, is independently selected from $C_{1-6}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rNR^{6a}R^{6a}$, $(CH_2)_rOH$, $(CH_2)_rOR^{6b}$, $(CH_2)_rSH$, $(CH_2)_rSR^{6b}$, $(CH_2)_rC(O)OH$, $(CH_2)_rC(O)R^{6b}$, $(CH_2)_rC(O)NR^{6a}R^{6a}$, $(CH_2)_rNR^{6d}C(O)R^{6a}$, $(CH_2)_rC(O)OR^{6b}$, $(CH_2)_rOC(O)R^{6b}$, $(CH_2)_rS(O)R^{6b}$, $(CH_2)_rS(O)_2R^{6b}$, $(CH_2)_rS(O)_2NR^{6a}R^{6a}$, $(CH_2)_rNR^{6d}S(O)_2R^{6b}$, and $(CH_2)_r$phenyl substituted with 0-3 $R^{6c}$;

with the proviso that if $R^6$ is attached to a carbon atom which also is attached to a nitrogen atom, or if two occurrences of $R^6$ are attached to the same carbon atom, then r contained within the definition of such $R^6$ must be greater than 0;

$R^{6a}$, at each occurrence, is independently selected from H, $C_{1-6}$ alkyl, $C_{3-6}$ cycloalkyl, and phenyl substituted with 0-3 $R^{6c}$;

$R^{6b}$, at each occurrence, is independently selected from $C_{1-6}$ alkyl, $C_{3-6}$ cycloalkyl, and phenyl substituted with 0-3 $R^{6c}$;

$R^{6c}$, at each occurrence, is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is independently selected from H, $C_{1-6}$ alkyl, and $C_{3-6}$ cycloalkyl;

$R^{11a}$ and $R^{12a}$, at each occurrence, are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, and $(CH_2)_r$phenyl substituted with 0-3 $R^{18}$;

with the proviso that if s is 1, then r contained within the definition of such $R^{11a}$ and $R^{12a}$ attached to carbon atoms bonded directly to Y must be greater than 0;

$R^{11b}$, $R^{12b}$, $R^{14a}$ and $R^{14b}$, at each occurrence, are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_qN(R^{18a})R^{18b}$, $(CH_2)_qOH$, $(CH_2)_qOR^{19}$, $(CH_2)_qSH$, $(CH_2)_q SR^{19}$, $(CH_2)_qC(O)OH$, $(CH_2)_qC(O)R^{19}$, $(CH_2)_rC(O)N(R^{18a})R^{18b}$, $(CH_2)_qN(R^{18c})C(O)R^{19}$, $(CH_2)_rC(O)OR^{19}$, $(CH_2)_qOC(O)R^{19}$, $(CH_2)_qS(O)R^{19}$, $(CH_2)_qS(O)_2R^{19}$, $(CH_2)_qS(O)_2N(R^{18a})R^{18b}$, $(CH_2)_qN(R^{18c})S(O)_2R^{19}$, and $(CH_2)_r$phenyl substituted with 0-3 $R^{18}$;

$R^{15}$, at each occurrence, is independently selected from $C_{1-8}$ alkyl, $(CH_2)_rC_{3-6}$ cycloalkyl, Cl, Br, I, F, $NO_2$, CN, $(CHR')_rNR^{15a}R^{15a}$, $(CHR')_rOH$, $(CHR')_rO(CHR')_rR^{15d}$, $(CHR')_rSH$, $(CHR')_rC(O)H$, $(CHR')_rS(CHR')_rR^{15d}$, $(CHR')_rC(O)OH$, $(CHR')_rC(O)(CHR')_rR^{15b}$, $(CHR')_rC(O)NR^{15a}R^{15a}$, $(CHR')_rNR^{15f}C(O)(CHR')_rR^{15b}$, $(CHR')_rNR^{15f}C(O)NR^{15f}R^{15f}$, $(CHR')_rC(O)O(CHR')_rR^{15d}$, $(CHR')_rOC(O)(CHR')_rR^{15b}$, $(CHR')_rC(=NR^{15f})NR^{15a}R^{15a}$, $(CHR')_rNHC(=NR^{15f})NR^{15f}R^{15f}$, $(CHR')_rS(O)(CHR')_rR^{15b}$, $(CHR')_rS(O)_2(CHR')_rR^{15b}$, $(CHR')_rS(O)_2NR^{15a}R^{15a}$, $(CHR')_rNR^{15f}S(O)_2(CHR')_rR^{15b}$, $C_{1-6}$ haloalkyl, $C_{2-8}$ alkenyl substituted with 0-3 R', $C_{2-8}$ alkynyl substituted with 0-3 R', $(CHR')_r$phenyl substituted with 0-3 $R^{15e}$, and a $(CH_2)_r$-5-10 membered heterocyclic system with 1-4 heteroatoms selected from N, O, and S, substituted with 0-2 $R^{15e}$;

R', at each occurrence, is independently selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{15e}$;

$R^{15a}$, at each occurrence, is independently selected from H, $C_{1-6}$ alkyl, $C_{2-8}$ alkenyl, $C_{2-8}$ alkynyl, a $(CH_2)_r$—$C_{3-10}$ carbocycle substituted with 0-5 $R^{15e}$, and a $(CH_2)_r$-5-10 membered heterocyclic system with 1-4 heteroatoms selected from N, O, and S, substituted with 0-2 $R^{15e}$;

$R^{15b}$, at each occurrence, is independently selected from $C_{1-6}$ alkyl, $C_{2-8}$ alkenyl, $C_{2-8}$ alkynyl, a $(CH_2)_r$—$C_{3-6}$ carbocycle substituted with 0-3 $R^{15e}$, and $(CH_2)_r$-5-6 membered heterocyclic system with 1-4 heteroatoms selected from N, O, and S, substituted with 0-2 $R^{15e}$;

$R^{15d}$, at each occurrence, is independently selected from $C_{2-8}$ alkenyl, $C_{2-8}$ alkynyl, $C_{1-6}$ alkyl substituted with 0-3 $R^{15e}$, a $(CH_2)_r$—$C_{3-10}$ carbocycle substituted with 0-3 $R^{15e}$, and a $(CH_2)_r$-5-6 membered heterocyclic system with 1-4 heteroatoms selected from N, O, and S, substituted with 0-3 $R^{15e}$;

$R^{15e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15f}$, and $(CH_2)_r$phenyl;

$R^{15f}$, at each occurrence, is independently selected from H, $C_{1-6}$ alkyl, $C_{3-6}$ cycloalkyl, and phenyl;

$R^{16}$, at each occurrence, is independently selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a}$, $(CHR')_rOH$, $(CHR')_rO(CHR')_rR^{16d}$, $(CHR')_rSH$, $(CHR')_rC(O)H$, $(CHR')_rS(CHR')_rR^{16d}$, $(CHR')_rC(O)OH$, $(CHR')_rC(O)(CHR')_rR^{16b}$, $(CHR')_rC(O)NR^{16a}R^{16a}$, $(CHR')_rNR^{16f}C(O)(CHR')_rR^{16b}$, $(CHR')_rC(O)O(CHR')_rR^{16d}$, $(CHR')_rOC(O)(CHR')_rR^{16b}$, $(CHR')_rC(=NR^{16f})NR^{16a}R^{16a}$, $(CHR')_rNHC(=NR^{16f})NR^{16f}R^{16f}$, $(CHR')_rS(O)(CHR')_rR^{16b}$, $(CHR')_rS(O)_2(CHR')_rR^{16b}$, $(CHR')_rS(O)_2NR^{16a}R^{16a}$, $(CHR')_rNR^{16f}S(O)_2(CHR')_rR^{16b}$, $C_{1-6}$ haloalkyl, $C_{2-8}$ alkenyl substituted with 0-3 R', $C_{2-8}$ alkynyl substituted with 0-3 R', and $(CHR')_r$phenyl substituted with 0-3 $R^{16e}$;

$R^{16a}$, at each occurrence, is independently selected from H, $C_{1-6}$ alkyl, $C_{2-8}$ alkenyl, $C_{2-8}$ alkynyl, a $(CH_2)_r$—$C_{3-10}$ carbocycle substituted with 0-5 $R^{16e}$, and a $(CH_2)_r$-5-10 membered heterocyclic system with 1-4 heteroatoms selected from N, O, and S, substituted with 0-2 $R^{16e}$;

$R^{16b}$, at each occurrence, is independently selected from $C_{1-6}$ alkyl, $C_{2-8}$ alkenyl, $C_{2-8}$ alkynyl, a $(CH_2)_rC_{3-6}$ carbocycle substituted with 0-3 $R^{16e}$, and a $(CH_2)_r$-5-6 membered heterocyclic system containing 1-4 heteroatoms selected from N, O, and S, substituted with 0-2 $R^{16e}$;

$R^{16d}$, at each occurrence, is independently selected from $C_{2-8}$ alkenyl, $C_{2-8}$ alkynyl, $C_{1-6}$ alkyl substituted with 0-3 $R^{16e}$, a $(CH_2)_r$—$C_{3-10}$ carbocycle substituted with 0-3 $R^{16e}$, and a $(CH_2)_r$-5-6 membered heterocyclic system with 1-4 heteroatoms selected from N, O, and S, substituted with 0-3 $R^{16e}$;

$R^{16e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$phenyl;

$R^{16f}$, at each occurrence, is independently selected from H, $C_{1-5}$ alkyl, and $C_{3-6}$ cycloalkyl, and phenyl;

$R^{18}$, at each occurrence, is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rS(O)C_{1-5}$ alkyl, $(CH_2)_rS(O)_2C_{1-5}$ alkyl, $(CH_2)_rS(O)_2N(R^{18a})R^{18b}$, $(CH_2)_rN(R^{18c})C(O)C_{1-5}$ alkyl $(CH_2)_rN(R^{18c})S(O)_2C_{1-5}$ alkyl, $(CH_2)_rC(O)N(R^{18a})R^{18b}$, $(CH_2)_rC(O)OC_{1-5}$ alkyl, $(CH_2)_rC(O)C_{1-5}$ alkyl, and $(CH_2)_rN(R^{18a})R^{18b}$;

$R^{18a}$, $R^{18b}$, and $R^{18c}$, at each occurrence, are independently selected from H, $C_{1-6}$ alkyl, and $C_{3-6}$ cycloalkyl;

alternatively, $R^{18a}$ and $R^{18b}$ along with the nitrogen to which both are attached form a pyrrolidine, piperidine, piperazine or morpholine ring;

$R^{19}$, at each occurrence, is independently selected from $C_{1-6}$ alkyl, $C_{3-6}$ cycloalkyl, and phenyl substituted with 0-3 $R^{18}$;

$R^{25}$, at each occurrence, is independently selected from H, $C_{1-6}$ alkyl, $C_{2-8}$ alkenyl, $C_{2-8}$ alkynyl, $(CH_2)_rC_{3-6}$ cycloalkyl, $(CH_2)_rC(O)R^{19}$, $(CH_2)_rC(O)N(R^{18a})R^{18b}$, $(CH_2)_rC(O)OR^{19}$, $(CH_2)_rS(O)_2R^{19}$, $(CH_2)_rS(O)_2N(R^{18a})R^{18b}$, and $(CH_2)_r$phenyl substituted with 0-3 $R^{18}$;

a is selected from 0 and 1;

b is selected from 0, and 2;

with the proviso that a+b is 2;

c is selected from 0, 1, and 2;

d is selected from 1, 2 and 3;

with the proviso that c+d is selected from 2, 3 or 4;

m is selected from 0, 1, and 2;

s is selected from 0 and 1;

with the proviso: m+s is selected from 0, 1, and 2;

v is selected from 0, 1, 2, and 3;

with the proviso: that the number of atoms in the shortest path linking the nitrogen to which $R^5$ is attached and the fused benzo or aromatic heterocyclic ring of B contained within such $R^5$ is less than or equal to 4;

r is selected from 0, 1, 2, 3, 4, and 5;

t is selected from 0, 1, 2, 3, 4, and 5;

q is selected from 1, 2, 3, 4, and 5; and u is selected from 0, 1 and, 2;

provided that when said compound is a compound of formula Ia; $R^1$ and $R^2$ are H or $C_{1-6}$ alkyl; $R^3$ is a mono or disubstituted $C_{1-6}$ alkyl, wherein the substituent is phenyl; phenyl or naphthyl; or mono, di or trisubstituted phenyl or naphthyl, wherein the substituents are hydroxy, $C_{1-3}$ alkyl, cyano, Cl, Br, I, F or trifluoromethyl; $R^6$ is $NR^{6a}R^{6a}$ or OH; $R^{6a}$ is H, $C_{1-6}$ alkyl, or phenyl substituted with 0-3 $R^{6c}$; $R^{6c}$ is $C_{1-3}$ alkyl, Cl, F, Br, I, CN, $CF_3$, or OH; and $R^4$ is absent, taken with the nitrogen to which it is attached to form an N-oxide, $C_{1-4}$ alkyl, or phenyl$C_{1-4}$ alkyl; and Z is not O.

2. The compound of claim 1, wherein $R^1$ and $R^2$ are independently selected from H and $C_{1-8}$ alkyl;

$R^4$ is absent, taken with the nitrogen to which it is attached to form an N-oxide, or selected from $C_{1-8}$ alkyl, $(CH_2)_rC_{3-6}$ cycloalkyl, and a $(CH_2)_r$—$C_{3-10}$ carbocycle substituted with 0-3 $R^{4c}$; and $R^{4c}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a}$, and $(CH_2)_r$phenyl.

3. The compound of claim 2, wherein

Z is O;

$R^6$, at each occurrence, is independently selected from $C_{1-4}$ alkyl, $(CH_2)_rC_{3-6}$ cycloalkyl, $(CH_2)_qNR^{6a}R^{6a}$, $(CH_2)_qOH$, $(CH_2)_qOR^{6b}$, $(CH_2)_rC(O)OH$, $(CH_2)_rC(O)R^{6b}$, (CH$_2$)$_r$C(O)NR$^{6a}$R$^{6a}$, (CH$_2$)$_q$NR$^{6d}$C(O)R$^{6a}$, (CH$_2$)$_r$S(O)$_2$NR$^{6a}$R$^{6a}$, (CH$_2$)$_r$NR$^{6d}$S(O)$_2$R$^{6b}$, and (CH$_2$)$_r$phenyl substituted with 0-3 R$^{6c}$;

R$^{6a}$, at each occurrence, is selected from H, methyl, ethyl, propyl, i-propyl, butyl, cyclopropyl, cyclopentyl, cyclohexyl, and phenyl;

R$^{6b}$, at each occurrence, is independently selected from methyl, ethyl, propyl, i-propyl, butyl, cyclopropyl, cyclopentyl, cyclohexyl, and phenyl;

R$^{6c}$, at each occurrence, is independently selected from C$_{1-6}$ alkyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, and (CH$_2$)$_r$NR$^{6d}$R$^{6d}$; and R$^{6d}$, at each occurrence, is independently selected from H, methyl, ethyl, propyl, i-propyl, butyl, cyclopropyl, cyclopentyl, and cyclohexyl.

4. The compound of claim 3, wherein

R$^3$ is selected from a (CR$^3$'H)$_r$—C$_{3-8}$ carbocycle substituted with 0-5 R$^{15}$, wherein the carbocycle is selected from phenyl, and naphthyl; and a (CR$^3$'H)$_r$-heterocyclic system substituted with 0-3 R$^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, indazolyl, isoindolyl, isothiadiazolyl, isoxazolyl, piperidinyl, pyrazolyl, 1,2,4-triazolyl, 1,2,3-triazolyl, tetrazolyl, thiadiazolyl, thiazolyl, oxazolyl, pyrazinyl, and pyrimidinyl; and R$^{5a}$ is selected from phenyl substituted with 0-5 R$^{16}$; and a heterocyclic system substituted with 0-3 R$^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrazolyl, 1,2,4-triazolyl, 1,2,3-triazolyl, tetrazolyl, thiadiazolyl, thiazolyl, oxazolyl, pyrazinyl, and pyrimidinyl.

5. A compound of formula (Ia):

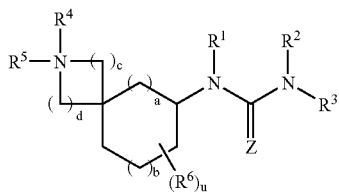

(Ia)

or stereoisomers of pharmaceutically accceptable salts thereof, wherein:

Z is O;

R$^1$ and R$^2$ are H;

R$^3$ is phenyl, naphthyl, pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, indazolyl, isoindolyl, isothiadiazolyl, isoxazolyl, piperidinyl, pyrazolyl, 1,2,4-triazolyl, 1,2,3-triazolyl, tetrazolyl, thiadiazolyl, thiazolyl, oxazolyl, pyrazinyl or pyrimidinyl, wherein the phenyl and naphthyl are substituted with 0-5 R$^{15}$ and the pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, indazolyl, isoindolyl, isothiadiazolyl, isoxazolyl, piperidinyl, pyrazolyl, 1,2,4-triazolyl, 1,2,3-triazolyl, tetrazolyl, thiadiazolyl, thiazolyl, oxazolyl, pyrazinyl and pyrimidinyl are substituted with 0-3 R$^{15}$;

R$^4$ is absent, taken with the nitrogen to which it is attached to form an N-oxide, or selected from C$_{1-8}$ alkyl, (CH$_2$)$_r$C$_{3-6}$ cycloalkyl, and a (CH$_2$)$_r$—C$_{3-10}$ carbocycle substituted with 0-3 R$^{4c}$;

R$^{4c}$, at each occurrence, is independently selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, (CH$_2$)$_r$NR$^{4a}$R$^{4a}$, and (CH$_2$)$_r$phenyl;

R$^5$ is selected from

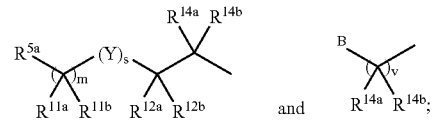

Y is selected from O, N(R$^{25}$), S, S(O), and S(O)$_2$;

ring B is a 5-7 membered cycloalkyl ring with containing a C═O, and being substituted with 0-2 R$^{11a}$, wherein the cycloalkyl ring is fused with a benzo group substituted with 0-3 R$^{16}$ or is fused with a 5-6 membered aromatic heterocyclic ring with 0-3 N, 0-1 O, or 0-1 S, the heterocyclic ring being substituted with 0-3 R$^{16}$;

alternatively, ring B is a 5-7 membered saturated heterocyclic ring with 0-1 O, N(R$^{25}$), S, S(O), and S(O)$_2$, substituted with 0-2 R$^{11a}$, wherein the heterocyclic ring is fused with a benzo group substituted with 0-3 R$^{16}$ or is fused with a 5-6 membered aromatic heterocyclic ring with 0-3 N, 0-1 O, or 0-1 S, the heterocyclic ring being substituted with 0-3 R$^{16}$;

provided that if ring B is a heterocyclic ring, then the number of carbon atoms separating the heteroatom of ring B and the nitrogen atom of formula (Ia) bonded to R$^5$ is at least 2;

R$^{5'}$ is selected from H, C$_{1-8}$ alkyl, C$_{2-8}$ alkenyl, C$_{2-8}$ alkynyl, (CH$_2$)$_r$C$_{3-6}$ cycloalkyl, (CH$_2$)$_q$C(O)R$^{4b}$, (CH$_2$)$_q$C(O)NR$^{4a}$R$^{4a}$, (CH$_2$)$_q$C(O)OR$^{4b}$, and a (CH$_2$)$_r$—C$_{3-10}$ carbocycle substituted with 0-3 R$^{4c}$;

alternatively, in formula (Ib), R$^5$ and R$^{5'}$ may together form a saturated ring containing 5 to 7 atoms optionally substituted with C$_{1-8}$ alkyl, C$_{2-8}$ alkenyl, C$_{2-8}$ alkynyl, (CH$_2$)$_r$ C$_{3-6}$ cycloalkyl, (CH$_2$)$_q$C(O)R$^{4b}$, (CH$_2$)$_q$C(O)NR$^{4a}$R$^{4a}$, (CH$_2$)$_q$C(O)OR$^{4b}$, (CH$_2$)$_r$—R$^{5a}$, or O—R$^{5a}$;

R$^{5a}$ is phenyl substituted with 1-3 R$^{16}$;

R$^6$, at each occurrence, is independently selected from C$_{1-4}$ alkyl, (CH$_2$)$_r$C$_{3-6}$ cycloalkyl, (CH$_2$)$_q$NR$^{6a}$R$^{6a}$, (CH$_2$)$_q$OH, (CH$_2$)$_q$OR$^{6b}$, (CH$_2$)$_r$C(O)OH, (CH$_2$)$_q$C(O)R$^{6b}$, (CH$_2$)$_r$C(O)NR$^{6a}$R$^{6a}$, (CH$_2$)$_q$NR$^{6d}$C(O)R$^{6a}$, (CH$_2$)$_r$S(O)$_2$NR$^{6a}$R$^{6a}$, (CH$_2$)$_r$NR$^{6d}$S(O)$_2$R$^{6b}$, and (CH$_2$)$_r$phenyl substituted with 0-3 R$^{6c}$;

R$^{6a}$, at each occurrence, is independently selected from H, methyl, ethyl, propyl, i-propyl, butyl, cyclopropyl, cyclopentyl, cyclohexyl, and phenyl;

R$^{6b}$, at each occurrence, is independently selected from methyl, ethyl, propyl, i-propyl, butyl, cyclopropyl, cyclopentyl, cyclohexyl, and phenyl;

R$^{6c}$, at each occurrence, is independently selected from C$_{1-6}$ alkyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, and (CH$_2$)$_r$NR$^{6d}$R$^{6d}$;

R$^{16d}$, at each occurrence, is independently selected from methyl, ethyl, propyl, i-propyl, butyl, cyclopropyl, cyclopentyl, and cyclohexyl.

$R^{11a}$ and $R^{12a}$, at each occurrence, are independently selected from H, $C_{1-6}$ alkyl, $C_{2-8}$ alkenyl, $C_{2-8}$ alkynyl, $(CH_2)_t C_{3-6}$ cycloalkyl, $(CF_2)_r CF_3$, $(CH_2)_r N(R^{18a})R^{18b}$, $(CH_2)_r OH$, $(CH_2)_r OR^{19}$, $(CH_2)_r SH$, $(CH_2)_r SR^{19}$, $(CH_2)_r C(O)OH$, $(CH_2)_r C(O)R^{19}$, $(CH_2)_r C(O)N(R^{18a})R^{18b}$, $(CH_2)_r N(R^{18c})C(O)R^{19}$, $(CH_2)_r C(O)OR^{19}$, $(CH_2)_r OC(O)R^{19}$, $(CH_2)_r S(O)R^{19}$, $(CH_2)_r S(O)_2 R^{19}$, $(CH_2)_r S(O)_2 N(R^{18a})R^{18b}$, $(CH_2)_r N(R^{18c})S(O)_2 R^{19}$, and $(CH_2)_t$ phenyl substituted with 0-3 $R^{18}$;

with the proviso that if s is 1, then r contained within the definition of such $R^{11a}$ and $R^{12a}$ attached to carbon atoms bonded directly to Y must be greater than 0;

$R^{11b}$, $R^{12b}$, $R^{14a}$ and $R^{14b}$, at each occurrence, are independently selected from H, $C_{1-6}$ alkyl, $C_{2-8}$ alkenyl, $C_{2-8}$ alkynyl, $(CH_2)_q C_{3-6}$ cycloalkyl, $(CF_2)_r CF_3$, $(CH_2)_q N(R^{18a}YR^{18b}$, $(CH_2)_q OH$, $(CH_2)_q OR^{19}$, $(CH_2)_q SH$, $(CH_2)_q SR^{19}$, $(CH_2)_r C(O)OH$, $(CH_2)_r C(O)R^{19}$, $(CH_2)_r C(O)N(R^{18a})R^{18b}$, $(CH_2)_q N(R^{18c})C(O)R^{19}$, $(CH_2)_r C(O)OR^{19}$, $(CH_2)_q OC(O)R^{19}$, $(CH_2)_q S(O)R^{19}$, $(CH_2)_q S(O)_2 R^{19}$, $(CH_2)_q S(O)_2 N(R^{18a})R^{18b}$, $(CH_2)_q N(R^{18c})S(O)_2 R^{19}$, and $(CH_2)_r$ phenyl substituted with 0-3 $R^{18}$;

$R^{15}$, at each occurrence, is independently selected from $C_{1-8}$ alkyl, $(CH_2)_r C_{3-6}$ cycloalkyl, Cl, Br, I, F, $NO_2$, CN, $(CHR')_r NR^{15a} R^{15a}$, $(CHR')_r OH$, $(CHR')_r O(CHR')_r R^{15d}$, $(CHR')_r SH$, $(CHR')_r C(O)H$, $(CHR')_r S(CHR')_r R^{15d}$, $(CHR')_r C(O)OH$, $(CHR')_r C(O)(CHR')_r R^{15b}$, $(CHR')_r C(O)NR^{15a} R^{15a}$, $(CHR')_r NR^{15f} C(O)$ $(CHR')_r R^{15b}$, $(CHR')_r NR^{15f} C(O)NR^{15f} R^{15f}$, $(CHR')_r C(O)O (CHR')_r R^{15d}$, $(CHR')_r OC(O)(CHR')_r R^{15b}$, $(CHR')_r C(=NR^{15f})NR^{15a} R^{15a}$, $(CHR')_r NHC(=NR^{15f}) NR^{15f} R^{15f}$, $(CHR')_r S(O)(CHR')_r R^{15b}$, $(CHR')_r S(O)_2 (CHR')_r R^{15b}$, $(CHR')_r S(O)_2 NR^{15a} R^{15a}$, $(CHR')_r NR^{15f} S (O)_2 (CHR')_r R^{15b}$, $C_{1-6}$ haloalkyl, $C_{2-8}$ alkenyl substituted with 0-3 R', $C_{2-8}$ alkynyl substituted with 0-3 R', $(CHR')_r$ phenyl substituted with 0-3 $R^{15e}$, and a $(CH_2)_r$-5-10 membered heterocyclic system containing 1-4 heteroatoms selected from N, O, and S, substituted with 0-2 $R^{15e}$;

R', at each occurrence, is independently selected from H, $C_{1-6}$ alkyl, $C_{2-8}$ alkenyl, $C_{2-8}$ alkynyl, $(CH_2)_r C_{3-6}$ cycloalkyl, and $(CH_2)_r$ phenyl substituted with $R^{15e}$;

$R^{15a}$, at each occurrence, is independently selected from H, $C_{1-6}$ alkyl, $C_{2-8}$ alkenyl, $C_{2-8}$ alkynyl, a $(CH_2)_r$—$C_{3-10}$ carbocycle substituted with 0-5 $R^{15e}$, and a $(CH_2)_r$-5-10 membered heterocyclic system containing 1-4 heteroatoms selected from N, O, and S, substituted with 0-2 $R^{15e}$;

$R^{15b}$, at each occurrence, is independently selected from $C_{1-6}$ alkyl, $C_{2-8}$ alkenyl, $C_{2-8}$ alkynyl, a $(CH_2)_r$—$C_{3-6}$ carbocycle substituted with 0-3 $R^{15e}$, and $(CH_2)_r$-5-6 membered heterocyclic system with 1-4 heteroatoms selected from N, O, and S, substituted with 0-2 $R^{15e}$;

$R^{15d}$, at each occurrence, is independently selected from $C_{2-8}$ alkenyl, $C_{2-8}$ alkynyl, $C_{1-6}$ alkyl substituted with 0-3 $R^{15e}$, a $(CH_2)_r$—$C_{3-10}$ carbocycle substituted with 0-3 $R^{15e}$, and a $(CH_2)_r$-5-6 membered heterocyclic system containing 1-4 heteroatoms selected from N, O, and S, substituted with 0-3 $R^{15e}$;

$R^{15e}$, at each occurrence, is independently selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{15f} R^{15f}$, and $(CH_2)_r$ phenyl;

$R^{15f}$, at each occurrence, is independently selected from H, $C_{1-6}$ alkyl, $C_{3-6}$ cycloalkyl, and phenyl;

$R^{16}$, at each occurrence, is independently selected from $C_{1-8}$ alkyl, $(CH_2)_r C_{3-6}$ cycloalkyl, $CF_3$, Cl, Br, I, F, $NR^{16a} R^{16a}$, $NO_2$, CN, OH, $OR^{16d}$, $C(O)R^{16b}$, $C(O)NR^{16a} R^{16a}$, and $NR^{16f} C(O)R^{16b}$;

$R^{6a}$, at each occurrence, is independently selected from H, methyl, ethyl, propyl, i-propyl, butyl, cyclopropyl, cyclopentyl, cyclohexyl, and $(CH_2)_r$ phenyl substituted with 0-3 $R^{16e}$;

$R^{16b}$, at each occurrence, is independently selected from methyl, ethyl, propyl, i-propyl, butyl, cyclopropyl, cyclopentyl, cyclohexyl, and $(CH_2)_r$ phenyl substituted with 0-3 $R^{16e}$;

$R^{16d}$, at each occurrence, is independently selected from methyl, ethyl, propyl, i-propyl, butyl, and phenyl;

$R^{16e}$, at each occurrence, is independently selected from methyl, ethyl, propyl, i-propyl, butyl, Cl, F, Br, I, CN, $NO_2$, $(CF_2)_r CF_3$, OH, and $(CH_2)_r OC_{1-5}$ alkyl;

$R^{16f}$, at each occurrence, is independently selected from H, methyl, ethyl, propyl, i-propyl, and butyl $R^{18}$, at each occurrence, is independently selected from $C_{1-6}$ alkyl, $C_{3-6}$ cycloalkyl, Cl, F, Br, I, CN, $NO_2$, $(CF_2)_r CF_3$, $(CH_2)_r OC_{1-5}$ alkyl, $(CH_2)_r OH$, $(CH_2)_r SC_{1-5}$ alkyl, $(CH_2)_r S(O)C_{1-5}$ alkyl, $(CH_2)_r S(O)_2 C_{1-5}$ alkyl, $(CH_2)_r S(O)_2 N(R^{18a})R^{18b}$, $(CH_2)_r N(R^{18c})C(O)C_{1-5}$ alkyl $(CH_2)_r N(R^{18c})S(O)_2 C_{1-5}$ alkyl, $(CH_2)_r C(O)N(R^{18a})R^{18b}$, $(CH_2)_r C(O)OC_{1-5}$ alkyl, $(CH_2)_r C(O)C_{1-5}$ alkyl, and $(CH_2)_r N(R^{18a})R^{18b}$;

$R^{18a}$, $R^{18b}$, and $R^{18c}$, at each occurrence, are independently selected from H, $C_{1-6}$ alkyl, and $C_{3-6}$ cycloalkyl;

alternatively, $R^{18a}$ and $R^{18b}$ along with the nitrogen to which both are attached form a pyrrolidine, piperidine, piperazine or morpholine ring;

$R^{19}$, at each occurrence, is independently selected from $C_{1-6}$ alkyl, $C_{3-6}$ cycloalkyl, and phenyl substituted with 0-3 $R^{18}$;

$R^{25}$, at each occurrence, is independently selected from H, $C_{1-6}$ alkyl, $C_{2-8}$ alkenyl, $C_{2-8}$ alkynyl, $(CH_2)_r C_{3-6}$ cycloalkyl, $(CH_2)_r C(O)R^{19}$, $(CH_2)_r C(O)N(R^{18a})R^{18b}$, $(CH_2)_r C(O)OR^{19}$, $(CH_2)_r S(O)_2 R^{19}$, $(CH_2)_r S(O)_2 N (R^{18a})R^{18b}$, and $(CH_2)_r$ phenyl substituted with 0-3 $R^{18}$;

a is selected from 0 and 1;

b is selected from 0, 1, and 2;

with the proviso that a+b is 2;

c is selected from 0 1, and 2;

d is selected from 1, 2 and 3;

with the proviso that c+d is 2, 3 and 4;

m is selected from 0, 1, and 2;

s is selected from 0 and 1;

with the proviso: m+s is selected from 0, 1, and 2;

v is selected from 0, 1, 2, and 3;

with the proviso: that the number of atoms in the shortest path linking the nitrogen to which $R^5$ is attached and the fused benzo or aromatic heterocyclic ring of B contained within such $R^5$ is less than or equal to 4;

r is selected from 0, 1, 2, 3, 4, and 5;

t is selected from 0, 1, 2, 3, 4, and 5;

q is selected from 1, 2, 3, 4, and 5; and u is selected from 0, 1 and, 2.

provided that provided that said compound is not a compound wherein: $R^3$ is mono, di or trisubstituted phenyl or naphthyl, wherein the substituents are hydroxy, $C_{1-3}$ alkyl, cyano, Cl, Br, I, F or trifluoromethyl; $R^6$ is $NR^{6a} R^{6a}$ or OH $R^{6a}$ is H, $C_{1-6}$ alkyl, or phenyl substituted with 0-3 $R^{6c}$; $R^{6c}$ is $C_{1-3}$ alkyl, Cl F Br I CN, $CF_3$, or OH; and $R^4$ is absent taken with the nitrogen to which it is attached to form an N-oxide, $C_{1-4}$ alkyl, or phenyl$C_{1-4}$ alkyl.

6. A compound of Table 1, wherein Table 1 is as follows:

TABLE 1

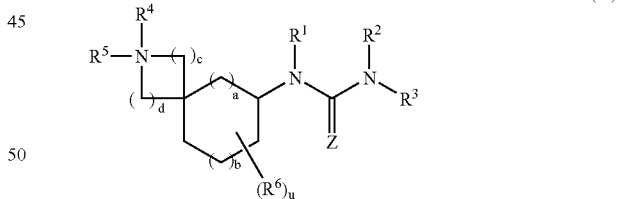

where a is 0 and b is 2;

| Example | c | d | $R^3$ | $R^5$ | Mass spec, $(M + H)^+$ |
|---|---|---|---|---|---|
| 1 | 1 | 3 | 3-(1-methyl-tetrazol-5-yl)-$C_6H_4$ | 4-F—$C_6H_4$—$(CH_2)_2$— | 492 |
| 2 | 1 | 3 | 3-(1-methyl-tetrazol-5-yl)-$C_6H_4$ | 4-F—$C_6H_4$—$CH_2$— | 478 |
| 3 | 2 | 2 | 3-(1-methyl-tetrazol-5-yl)-$C_6H_4$ | 4-F—$C_6H_4$—$(CH_2)_3$— | 506 |
| 4 | 2 | 2 | 3-(1-methyl-tetrazol-5-yl)-$C_6H_4$ | 4-F—$C_6H_4$—$(CH_2)_2$— | 492 |
| 5 | 2 | 2 | 3-(1-methyl-tetrazol-5-yl)-$C_6H_4$ | 4-Cl—$C_6H_4$—$(CH_2)_2$— | 508 |
| 6 | 2 | 2 | 3-(1-methyl-tetrazol-5-yl)-$C_6H_4$ | $C_6H_4$—$(CH_2)_3$— | 488 |
| 7 | 2 | 2 | 3-(1-methyl-tetrazol-5-yl)-$C_6H_4$ | 2,4-$Cl_2$—$C_6H_4$—$(CH_2)_2$— | 542 |
| 8 | 2 | 2 | 3-(1-methyl-tetrazol-5-yl)-$C_6H_4$ | $C_6H_4$—CH=$CHCH_2$— | 486 |
| 9 | 2 | 2 | 3-(1-methyl-tetrazol-5-yl)-$C_6H_4$ | 4-Cl—$C_6H_4$—$(CH_2)_3$— | 522 |
| 10 | 1 | 3 | 4-methyl-5-acetylthiazol-2-yl | 4-F—$C_6H_4$—$(CH_2)_2$— | 473 |
| 11 | 1 | 3 | 3-ethyl-5-(1-methyl-tetrazol-5-yl)-$C_6H_4$ | 4-F—$C_6H_4$—$(CH_2)_2$— | 520 |
| 12 | 1 | 3 | 3-ethyl-5-(1-methyl-tetrazol-5-yl)-$C_6H_4$ | 4-F—$C_6H_4$—$CH_2$— | 506 |
| 13 | 1 | 3 | 4-methyl-5-acetylthiazol-2-yl | 4-F—$C_6H_4$—$CH_2$— | 459 |

7. The compound of claim 1, wherein $R^4$ is absent; $R^5$ is

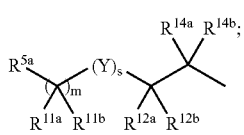

$R^{11a}$ and $R^{12a}$, at each occurrence, are independently selected from H, methyl, ethyl, propyl, i-propyl, butyl, pentyl, hexyl, cyclopropyl, cyclopentyl, cylohexyl, $CF_3$, $(CH_2)_rN(R^{18a})R^{18b}$, $(CH_2)_rOH$;

$R^{11b}$, $R^{12b}$, $R^{14a}$ and $R^{14b}$, at each occurrence, are independently selected from H, methyl, ethyl, propyl, i-propyl, butyl, pentyl, hexyl, cyclopropyl, cyclopentyl, cylohexyl, $CF_3$, $(CH_2)_qN(R^{18a})R^{18b}$, $(CH_2)_qOH$;

$R^{25}$ at each occurrence, is independently selected from H, methyl, ethyl, propyl, i-propyl, butyl, cyclopropyl, cyclopentyl, cyclohexyl, $(CH_2)_rC(O)R^{19}$, $(CH_2)_rC(O)N(R^{18a})R^{18b}$, $(CH_2)_rC(O)OR^{19}$, and $(CH_2)_r$phenyl substituted with 0-3 $R^{18}$.

8. A compound of formula (Ia):

(Ia)

or stereoisomers of pharmaceutically accceptable salts thereof, wherein:

Z is O;

$R^1$ and $R^2$ are H; $C_{1-8}$ alkyl, $C_{2-8}$ alkenyl, and $C_{2-8}$ alkyl;

$R^3$ is selected from a $(CR^{3'}R^{3'})_r$—$C_{3-10}$ carbocycle substituted with 0-5 $R^{15}$ and a $(CR^{3'}R^{3'})_r$-5-10 membered heterocyclic system with 1-4 heteroatoms selected from N, O, and S, substituted with 0-3 $R^{15}$;

$R^{3'}$, at each occurrence, is independently selected from H, $C_{1-6}$ alkyl, $(CH_2)_rC_{3-6}$ cycloalkyl, and phenyl;

R$^4$ is absent,
R$^5$ is

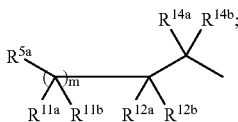

R$^{5a}$ is selected from a C$_{3-10}$ carbocycle substituted with 0-5 R$^{16}$, and a 5-10 membered heterocyclic system with 1-4 heteroatoms selected from N, O, and S, substituted with 0-3 R$^{16}$;

R$^6$, at each occurrence, is independently selected from C$_{1-6}$ alkyl, C$_{2-8}$ alkenyl, C$_{2-8}$ alkynyl, (CH$_2$)$_r$C$_{3-6}$ cycloalkyl, (CF$_2$)$_r$CF$_3$, CN, (CH$_2$)$_r$NR$^{6a}$R$^{6a}$, (CH$_2$)$_r$OH, (CH$_2$)$_r$OR$^{6b}$, (CH$_2$)$_r$SH, (CH$_2$)$_r$SR$^{6b}$, (CH$_2$)$_r$C(O)OH, (CH$_2$)$_r$C(O)R$^{6b}$, (CH$_2$)$_r$C(O)NR$^{6a}$R$^{6a}$, (CH$_2$)$_r$NR$^{6d}$C(O)R$^{6a}$, (CH$_2$)$_r$C(O)OR$^{6b}$, (CH$_2$)$_r$OC(O)R$^{6b}$, (CH$_2$)$_r$S(O)R$^{6b}$, (CH$_2$)$_r$S(O)$_2$R$^{6b}$, (CH$_2$)$_r$S(O)$_2$NR$^{6a}$R$^{6a}$, (CH$_2$)$_r$NR$^{6d}$S(O)$_2$R$^{6b}$, and (CH$_2$)$_r$phenyl substituted with 0-3 R$^{6c}$;

with the proviso that if R$^6$ is attached to a carbon atom which also is attached to a nitrogen atom, or if two occurrences of R$^6$ are attached to the same carbon atom, then r contained within the definition of such R$^6$ must be greater than 0;

R$^{6a}$, at each occurrence, is independently selected from H, C$_{1-6}$ alkyl, C$_{3-6}$ cycloalkyl, and phenyl substituted with 0-3 R$^{6c}$;

R$^{6b}$, at each occurrence, is independently selected from C$_{1-6}$ alkyl, C$_{3-6}$ cycloalkyl, and phenyl substituted with 0-3 R$^{6c}$;

R$^{6c}$, at each occurrence, is independently selected from C$_{1-6}$ alkyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, and (CH$_2$)$_r$NR$^{6d}$R$^{6d}$;

R$^{6d}$, at each occurrence, is independently selected from H, C$_{1-6}$ alkyl, and C$_{3-6}$ cycloalkyl;

R$^{11a}$ and R$^{12a}$, at each occurrence, are independently selected from H, methyl, ethyl and OH;

R$^{11b}$, R$^{12b}$, R$^{14a}$, and R$^{14b}$, at each occurrence, are independently selected from H, methyl and ethyl;

R$^{15}$, at each occurrence, is independently selected from C$_{1-8}$ alkyl, (CH$_2$)$_r$C$_{3-6}$ cycloalkyl, Cl, Br, I, F, NO$_2$, CN, (CHR')$_r$NR$^{15a}$R$^{15a}$, (CHR')$_r$OH, (CHR')$_r$O(CHR')$_r$R$^{15d}$, (CHR')$_r$SH, (CHR')$_r$C(O)H, (CHR')$_r$S(CHR')$_r$R$^{15d}$, (CHR')$_r$C(O)OH, (CHR')$_r$C(O)(CHR')$_r$R$^{15b}$, (CHR')$_r$C(O)NR$^{15a}$R$^{15a}$, (CHR')$_r$NR$^{15f}$C(O) (CHR')$_r$R$^{15b}$, (CHR')$_r$NR$^{15f}$C(O)NR$^{15f}$R$^{15f}$, (CHR')$_r$C(O)O(CHR')$_r$R$^{15d}$, (CHR')$_r$OC(O)(CHR')$_r$R$^{15b}$, (CHR')$_r$C(=NR$^{15f}$)NR$^{15a}$R$^{15a}$, (CHR')$_r$NHC(=NR$^{15f}$)NR$^{15f}$R$^{15f}$, (CHR')$_r$S(O)(CHR')$_r$R$^{15b}$, (CHR')$_r$S(O)$_2$(CHR')$_r$R$^{15b}$, (CHR')$_r$S(O)$_2$NR$^{15a}$R$^{15a}$, (CHR')$_r$NR$^{15f}$S(O)$_2$(CHR')$_r$R$^{15b}$, C$_{1-6}$ haloalkyl, C$_{2-8}$ alkenyl substituted with 0-3 R', C$_{2-8}$ alkynyl substituted with 0-3 R', (CHR')$_r$phenyl substituted with 0-3 R$^{15e}$, and a (CH$_2$)$_r$-5-10 membered heterocyclic system containing 1-4 heteroatoms selected from N, O, and S, substituted with 0-2 R$^{15e}$;

R', at each occurrence, is independently selected from H, C$_{1-6}$ alkyl, C$_{2-8}$ alkenyl, C$_{2-8}$ alkynyl, (CH$_2$)$_r$C$_{3-6}$ cycloalkyl, and (CH$_2$)$_r$phenyl substituted with R$^{15e}$;

R$^{15a}$, at each occurrence, is independently selected from H, C$_{1-6}$ alkyl, C$_{2-8}$ alkenyl, C$_{2-8}$ alkynyl, a (CH$_2$)$_r$—C$_{3-10}$ carbocycle substituted with 0-5 R$^{15e}$, and a (CH$_2$)$_r$-5-10 membered heterocyclic system containing 1-4 heteroatoms selected from N, O, and S, substituted with 0-2 R$^{15e}$;

R$^{15b}$, at each occurrence, is independently selected from C$_{1-6}$ alkyl, C$_{2-8}$ alkenyl, C$_{2-8}$ alkynyl, a (CH$_2$)$_r$—C$_{3-6}$ carbocycle substituted with 0-3 R$^{15e}$, and (CH$_2$)$_r$-5-6 membered heterocyclic system with 1-4 heteroatoms selected from N, O, and S, substituted with 0-2 R$^{15e}$;

R$^{15d}$, at each occurrence, is independently selected from C$_{2-8}$ alkenyl, C$_{2-8}$ alkynyl, C$_{1-6}$ alkyl substituted with 0-3 R$^{15e}$, a (CH$_2$)$_r$—C$_{3-10}$ carbocycle substituted with 0-3 R$^{15e}$, and a (CH$_2$)$_r$,5-6 membered heterocyclic system containing 1-4 heteroatoms selected from N, O, and S, substituted with 0-3 R$^{15e}$;

R$^{15e}$, at each occurrence, is independently selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{15f}$R$^{15f}$, and (CH$_2$)$_r$phenyl;

R$^{15f}$, at each occurrence, is independently selected from H, C$_{1-6}$ alkyl, C$_{3-6}$ cycloalkyl, and phenyl;

R$^{16}$, at each occurrence, is independently selected from Cl, F, CF$_3$, and CN;

R$^{18}$, at each occurrence, is independently selected from C$_{1-6}$ alkyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, (CH$_2$)$_r$S(O)C$_{1-5}$ alkyl, (CH$_2$)$_r$S(O)$_2$C$_{1-5}$ alkyl, (CH$_2$)$_r$S(O)$_2$N(R$^{18a}$)R$^{18b}$, (CH$_2$)$_r$N(R$^{18c}$)C(O)C$_{1-5}$ alkyl (CH$_2$)$_r$N(R$^{18c}$)S(O)$_2$C$_{1-5}$ alkyl, (CH$_2$)$_r$C(O)N(R$^{18a}$)R$^{18b}$, (CH$_2$)$_r$C(O)OC$_{1-5}$ alkyl, (CH$_2$)$_r$C(O)C$_{1-5}$ alkyl, and (CH$_2$)$_r$N(R$^{18a}$)R$^{18b}$;

R$^{18a}$, R$^{18b}$, and R$^{18c}$, at each occurrence, are independently selected from H, C$_{1-6}$ alkyl, and C$_{3-6}$ cycloalkyl;

alternatively, R$^{18a}$ and R$^{18b}$ along with the nitrogen to which both are attached form a pyrrolidine, piperidine, piperazine or morpholine ring;

R$^{19}$, at each occurrence, is independently selected from C$_{1-6}$ alkyl, C$_{3-6}$ cycloalkyl, and phenyl substituted with 0-3 R$^{18}$;

R$^{25}$, at each occurrence, is independently selected from H, methyl, ethyl, propyl, i-propyl, butyl, cyclopropyl,cyclopentyl, cyclohexyl, (CH$_2$)$_r$C(O)R$^{19}$, (CH$_2$)$_r$C(O)N(R$^{18a}$)R$^{18b}$, (CH$_2$)$_r$C(O)OR$^{19}$, and (CH$_2$)$_r$phenyl substituted with 0-3 R$^{18}$.

a is selected from 0 and 1;

b is selected from 0, 1, and 2;

with the proviso that a+b is 2;

c is selected from 0 1, and 2;

d is selected from 1, 2 and 3;

with the proviso that c+d is 2, 3 and 4;

m is selected from 0, 1, and 2;

r is selected from 0 , 1, 2, 3, 4, and 5;

q is selected from 1, 2, 3, 4, and 5; and u is selected from 0, 1 and, 2;

provided that said compound is not a compound wherein; R$^1$ and R$^2$ are H or C$_{1-6}$ alkyl; R$^3$ is a mono or disubstituted C$_{1-6}$ alkyl, wherein the substituent is phenyl; phenyl or naphthyl or mono, di or trisubstituted phenyl or naphthyl, wherein the substituents are hydroxy, C$_{1-3}$ alkyl, cyano, Cl, Br, I, F or trifluoromethyl; R$^6$ is NR$^{6a}$R$^{6a}$ or OH; R$^{6a}$ is H, C$_{1-6}$ alkyl, or phenyl substituted with 0-3 R$^{6c}$; R$^{6c}$ is C$_{1-3}$ alkyl, Cl, F, Br, I, CN, CF$_3$, or OH.

9. The compound of claim 1, wherein $R^5$ is

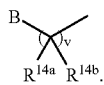

10. A pharmaceutical composition, comprising a pharmaceutically acceptable carrier and a therapeutically effective amount of a compound according to claim 1, or a pharmaceutically acceptable salt thereof.

11. A pharmaceutical composition, comprising a pharmaceutically acceptable carrier and a therapeutically effective amount of a compound according to claim 6, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 7,479,496 B2 |
| APPLICATION NO. | : 11/060246 |
| DATED | : January 20, 2009 |
| INVENTOR(S) | : Douglas G. Batt et al. |

Page 1 of 3

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 888 days.

Cover Page, Column 2 (Other Publications)
Line 7, "Indentification" should read -- Identification --.

Cover Page, Column 2 (Abstract)
Line 7, before "in the specification." delete -- herein --.

Column 1
Line 4, Please insert the following heading under the title of the invention: -- CROSS-REFERENCE TO RELATED APPLICATION --.

Column 53
Line 51, after "cycloalkyl ring" delete "with containing" and insert -- optionally with --.

Column 55
Line 22, "$C_1$," should read -- Cl, --;
Line 50, "containing" should read -- with --;
Line 56, "$(CH_2)_r$-5$^{-6}$" should read -- $(CH_2)_r$-5-6 --.

Column 56
Line 3, "$C_{1-5}$ alkyl" should read -- $C_{1-5}$ alkyl, --;
Line 21, after "0," insert -- 1 --;
Line 38, "and," should read -- and --.

Signed and Sealed this
Twenty-fifth Day of January, 2011

David J. Kappos
*Director of the United States Patent and Trademark Office*

CERTIFICATE OF CORRECTION (continued)

Column 57
Line 4, after "is" insert -- independently --;
Line 12, "(CH$_2$)$_r$OC$_1$-5 alkyl," should read -- (CH$_2$)$_r$OC$_{1-5}$ alkyl, --;
Line 42, "(Ia))" should read -- (Ia) --;
Line 51, "of" should read -- or --;
Line 51, "accceptable" should read -- acceptable --.

Column 58
Line 21, after "cycloalkyl ring" delete "with containing" and insert -- optionally with --;
Line 43, "containing" should read -- with --;
Line 63, "(CH$_2$)$_r$ OC$_1$-5 alkyl," should read -- (CH$_2$)$_r$OC$_{1-5}$ alkyl, --;
Line 65, "R$^{16d}$," should read -- R$^{6d}$, --;
Line 65, after "from" insert -- H, --;
Line 67, "cyclohexyl." should read -- cyclohexyl; --.

Column 59
Lines 15-16, "(CH$_2$)$_q$N(R$^{18a}$YR$^{18b}$," should read -- (CH$_2$)$_q$N(R$^{18a}$)R$^{18b}$, --;
Line 36, "containing" should read -- with --;
Line 45, "containing" should read -- with --;
Line 57, "containing" should read -- with --.

Column 60
Line 3, "R$^{6a}$," should read -- R$^{16a}$, --;
Line 17, "butyl" should read -- butyl; --;
Line 22, "C$_1$-5 alkyl" should read -- C$_{1-5}$ alkyl, --;
Line 43, "0 1," should read -- 0, 1 --;
Line 45, "and" should read -- or --;
Line 58, "and, 2." should read -- and 2; --;
Line 59, after "provided that" delete "provided that"; (Second Occurrence)
Line 63, "OH" should read -- OH; --;
Line 64, "Cl F Br I" should read -- Cl, F, Br, I, --;
Line 65, "absent" should read -- absent, --.

Column 61-62
Line 38, after "Table" insert -- . --.

Column 61
Lines 40-67, delete "The compound of claim 1, wherein R$^4$ is absent; R$^5$ is

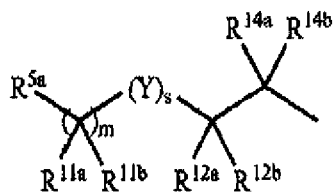

$R^{11a}$ and $R^{12a}$, at each occurrence, are independently selected from H, methyl, ethyl, propyl, i-propyl,
   butyl, pentyl, hexyl, cyclopropyl, cyclopentyl, cylohexyl, $CF_3$, $(CH_2)_rN(R^{18a})R^{18b}$, $(CH_2)_rOH$;
$R^{11b}$, $R^{12b}$, $R^{14a}$ and $R^{14b}$, at each occurrence, are independently selected from H, methyl,
   ethyl, propyl, i-propyl, butyl, pentyl, hexyl, cyclopropyl, cyclopentyl, cylohexyl, $CF_3$,
   $(CH_2)_qN(R^{18a})R^{18b}$, $(CH_2)_qOH$;
$R^{25}$ at each occurrence, is independently selected from H, methyl, ethyl, propyl, i-propyl,
   butyl, cyclopropyl, cyclopentyl, cyclohexyl, $(CH_2)_rC(O)R^{19}$, $(CH_2)_rC(O)N(R^{18a})R^{18b}$,
   $(CH_2)_rC(O)OR^{19}$, and $(CH_2)_r$phenyl substituted with 0-3 $R^{18}$." and insert
-- The compound of claim 1, wherein $R^4$ is absent;
$R^5$ is

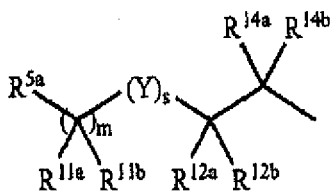

$R^{11a}$ and $R^{12a}$, at each occurrence, are independently selected from H, methyl, ethyl, propyl, i-propyl,
   butyl, pentyl, hexyl, cyclopropyl, cyclopentyl, cylohexyl, $CF_3$, $(CH_2)_rN(R^{18a})R^{18b}$, $(CH_2)_rOH$;
$R^{11b}$, $R^{12b}$, $R^{14a}$ and $R^{14b}$, at each occurrence, are independently selected from H, methyl,
   ethyl, propyl, i-propyl, butyl, pentyl, hexyl, cyclopropyl, cyclopentyl, cylohexyl,
   $CF_3$, $(CH_2)_qN(R^{18a})R^{18b}$, $(CH_2)_qOH$;
$R^{25}$, at each occurrence, is independently selected from H, methyl, ethyl, propyl, i-propyl,
   butyl, cyclopropyl, cyclopentyl, cyclohexyl, $(CH_2)_rC(O)R^{19}$, $(CH_2)_rC(O)N(R^{18a})R^{18b}$,
   $(CH_2)_rC(O)OR^{19}$, and $(CH_2)_r$phenyl substituted with 0-3 $R^{18}$. --, therefor.

Column 62
Line 57, "of" should read -- or --;
Line 57, "accceptable" should read -- acceptable --;
Line 60, "are H;" should read -- are independently selected from H, --;
Line 60, "$C_{2-8}$ alkyl;" should read -- $C_{2-8}$ alkynyl; --.

Column 63
Line 59, "containing" should read -- with --.

Column 64
Lines 1, "containing" should read -- with --;
Line 13, "containing" should read -- with --;
Line 23, after "from" insert -- methyl, --;
Line 29, "$C_{1-5}$ alkyl" should read -- $C_{1-5}$ alkyl, --;
Lines 43-44, "cyclopropyl,cyclopentyl," should read -- cyclopropyl, cyclopentyl, --;
Line 46, "0-3 $R^{18}$." should read -- 0-3 $R^{18}$; --;
Line 51, "0 1," should read -- 0, 1 --;
Line 53, after "is" insert -- selected from --;
Line 57, "and," should read -- and --;
Line 62, "naphthyl" should read -- naphthyl; --.